(12) United States Patent
Westesen et al.

(10) Patent No.: US 6,197,349 B1
(45) Date of Patent: Mar. 6, 2001

(54) PARTICLES WITH MODIFIED PHYSICOCHEMICAL PROPERTIES, THEIR PREPARATION AND USES

(75) Inventors: Kirsten Westesen, Königslutter (DE); Britta Siekmann, Södertälje (SE)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/968,899

(22) Filed: Nov. 6, 1997

Related U.S. Application Data

(63) Continuation of application No. 08/591,582, filed as application No. PCT/SE94/00728 on Aug. 9, 1994, now abandoned.

(30) Foreign Application Priority Data

Aug. 12, 1993 (DE) .................................... 43 27 063

(51) Int. Cl.$^7$ .............................. A61K 9/50; A61K 47/30; B32B 5/16; B01J 13/02
(52) U.S. Cl. ..................... 424/501; 424/502; 514/772.3; 427/213.36; 428/402.21; 264/4.1; 264/4.3; 264/4.33; 264/4.4
(58) Field of Search .................... 424/489, 464, 424/502, 501; 427/213.31, 213.36; 514/772.3; 428/402.21; 264/4.1, 4.3, 4.33, 4.4

(56) References Cited

U.S. PATENT DOCUMENTS 4,540,602 * 9/1985 Motoyama et al. ............ 427/213.31

FOREIGN PATENT DOCUMENTS 3 524 788 1/1987 (DE) .
61-68412 4/1986 (JP) .

OTHER PUBLICATIONS

Westesen, K. et al., "Investigations on the physical state of lipid nanoparticles by synchrotron radiation X-ray diffraction", *International Journal of Pharmaceutics*, vol. 93, 1993, pp. 189–199.

Sjostrom, B. et al., "Preparation of submicron drug particles in lecithin–stabilized o/w emulsions. II. Characterization of cholesteryl acetate particles", *International Journal of Pharmaceutics*, vol. 94, 1993, pp. 89–101.

Kawashima, Y. et al., "Preparation of powdered phospholipid nanospheres by spray drying in an aqueous system with sugars", *Chem. Pharm. Bull.*, Japan, 1992.

Ford, J.L. et al., "The properties of solid dispersions of indomethacin or phenylbutazone in polyethylene glycol", *Int. J. Pharm.*, Netherlands, 1986.

* cited by examiner

Primary Examiner—Carlos A. Azpuru
(74) Attorney, Agent, or Firm—Keil & Weinkauf

(57) ABSTRACT

Particles comprising (a) a supercooled melt of a poorly water-soluble substance and (b) a stabilizing agent, which have a mean particle size of between 30 and 500 nm, and disperse compositions containing them, as administration forms and delivery systems for drugs, vaccines and other biologically active agents such as herbicides, pesticides, insecticides, fungicides, fertilizers, vitamins, nutrition additives and cosmetics.

17 Claims, 7 Drawing Sheets

PARTICLES WITH MODIFIED PHYSICOCHEMICAL PROPERTIES, THEIR PREPARATION AND USES

CROSS-REFERENCE TO RELATED APPLICATION(S)

This is a Continuation Application of Application Ser. No. 08/591,582, filed on Feb. 07, 1996, which is a National Stage Application under 35 U.S.C. 371, based on International Application No. PCT/SE 94/00,728, filed Aug. 09, 1994 now abandoned.

FIELD OF THE INVENTION

The present invention is in the area of administration forms and delivery systems for drugs, vaccines and other biologically active agents such as herbicides. pesticides, insecticides, fungicides, fertilizers. vitamins, nutrition additives and cosmetics. More specifically, the invention is related to particles comprising an interior phase of ubidecarenone or of other poorly water-soluble substances characterized in that these substances, which are solid and primarily crystalline at room temperature in the bulk phase, are primarily present in an amorphous, preferably liquid, physical state in the particles, e.g. as a supercooled melt, hereinafter being referred to as particles of supercooled melts (PSM); to fine dispersions of PSMs in a dispersion medium of pharmaceutically acceptable liquids, preferably aqueous media; as well as to the method of manufacture and the use of such particles and dispersions as delivery systems for the parenteral, enteral, peroral, oral, nasal, pulmonal, ophthalmic, mucosal or (trans)dermal administration of poorly water-soluble bioactive agents, particularly drugs; and to their use in cosmetic, food and agricultural products.

BACKGROUND OF THE INVENTION

Numerous poorly water-soluble bioactive substances, e.g. drugs, are present as solid, in particular crystalline bulk materials at room temperature, primarily in the form of poorly wettable powders with grain sizes in the micro- and millimeter size range. In many cases drugs which share these properties exhibit a poor bioavailability, particularly upon peroral administration. Bioavailability is defined as the rate and the extent of absorption of a bioactive agent into the blood compartment and of the distribution to its site of action. The low absorption rate of poorly water-soluble, in particular lipophilic substances from the gastrointestinal tract (GIT) is generally attributed to the poor solubility of these substances and to their poor wettability in gastrointestinal fluids. Industrially manufactured bioactive substances have generally particle sizes well above 1 μm since they are preferably processed from cruder materials by mechanical comminution such as milling and micronization. In some cases precipitation from organic solvents is applied. Sjöström et al. (Sjöström B., Kronberg B., Carlfors J., J. Pharm. Sci. 82 (1993) 579–583) describe the manufacturing of submicron drug particles by precipitation in solvent containing o/w emulsions. The method is based on the use of potentially harmful organic solvents such as toluene and chlorinated hydrocarbons. From the technical point, it is virtually impossible to completely remove the solvents from the product so that the solid drug particles contain solvent residues which present a toxicological risk. Moreover, the use of volatile and inflammable organic solvents requires special precautions with respect to manufacturing safety.

Direct injection into the bloodstream (in an aqueous vehicle) is not possible with many drugs due to the poor aqueous solubility of these substances. The size of suspended, poorly water-soluble drug particles/aggregates is generally too large for intravenous administration because it exceeds the diameter of the smallest blood capillaries and would thus lead to capillary blockage and embolism.

In case of extravasal administration of solid drugs with the objective of a systemic drug action, the dissolution process of the substance can become the rate limiting step in absorption and might thus lead to a poor bioavailability. It is common knowledge that the dissolution rate of a substance is affected inter alia by its particle size, its wettability and with crystalline substances also by the energy required to overcome lattice forces. It can therefore be deduced that the bioavailability of poorly water-soluble bioactive agents can in principle be enhanced by the following three technological manipulations:

reduction of particle size, hydrophilization of particle surfaces to improve the wettability in aqueous media, and reduction of the crystallinity of the substance.

For example, improvement of the bioavailability after peroral administration due to enhancement of the rate of dissolution by micronization has been described for digoxin (Shaw, T. R. D., Carless. J. E., Europ. J. Clin. Pharmacol., 7 (1974) 269) und griseofulvin (Atkinson, R. M., Bedford, C., Child, K. J., Tomich, E. G., Nature 193 (1962) 588). Micronization is the comminution of agglomerates to microcrystals of a size between 1 and 30 μm by means of appropriate comminution equipment such as vibration mills, fluid-energy mills and colloid mills. Micronized substances can, however, exhibit wettability problems, e.g. due to aerophilization during the milling process. The reduced wettability counteracts to the increased dissolution rate achievable by micronization as a result of the reduced particle size and can therefore lead to a reduced dissolution rate.

A further reduction from the micrometer to the nanometer size range, e.g. in order to further enhance the bioavailability or to render possible parenteral, in particular intravenous administration, is practically not feasible with the conventional equipment used for micronization or requires a tremendous technological effort, and is therefore extremely costly and in many cases ineffective. Additionally, the reduction of solids to submicron-sized powders can bring about heavy difficulties in handling of these dry products such as an increased risk of dust explosions and cross-contamination problems in a factory environment. Moreover, such systems present a risk to health for persons exposed to the possible inhalation and absorption of potent bioactive materials.

For many applications there is, however, an obvious need to reduce the particle size down to the nanometer range. Thus particle size is an important factor with respect to the parenteral, in particular intravenous administration of drugs. As already mentioned before, many lipophilic drugs can not be formulated as aqueous solutions due to their low aqueous solubility. Intravenous administration of suspensions to sparingly soluble substances in water bears the risk of capillary blockage and embolism since the suspended particles are generally larger than the smallest blood vessels.

So far there are basically only two possible ways of intravenously administering such lipophilic drugs. One possibility is to solubilize the drug in an aqueous medium by use of solubilizing agents such as surfactants and organic solvents. Although the use of these agents may increase the solubility of lipophilic substances to such an extent that therapeutic doses can be achieved, these systems have some considerable disadvantages. Intravenous administration of organic or alcoholic solutions is often associated with pain and local thrombophiebetis at the injection site. The use of high surfactant concentrations, which often are necessary for solubilization, can cause anaphylactoid reactions including anaphylactic shock, and is thus not advisable.

The second possibility is incorporation of poorly water soluble substances into colloidal drug carrier systems. Colloidal carrier systems comprise e.g. polymeric (micro- and) nanoparticles, liposomes, lipid emulsions and lipid suspensions. These drug carriers are vehicles of predominantly colloidal size, i.e. in the nanometer size range, in which the drug is incorporated. Due to their surface characteristics these vehicles can be dispersed in an aqueous medium. Since their size is—with the exception of microparticles—below 1 $\mu$m, they are suited for intravenous administration.

Drug carrier systems in the micrometer size range are represented by microspheres consisting of a solid polymer matrix, and microcapsules in which a liquid or a solid phase is surrounded and encapsulated by a polymer film. Nanoparticles consist, like microspheres, of a solid polymer matrix, however their mean particle size lies in the nanometer range. Both micro- and nanoparticles are generally prepared either by emulsion polymerization or by solvent evaporation techniques. Due to these production methods, micro- and nanoparticles bear the risk of residual contaminations from the production process like organic solvents such as chlorinated hydrocarbons, as well as toxic monomers, surfactants and cross-linking agents which can lead to toxicological problems. Moreover, some polymeric materials such as polylactic acid and polylactic-glycolic acid degrade very slowly in vivo so that multiple administration could lead to polymer accumulation associated with adverse side effects. Other polymers such as polyaikylcyanoacrylates release toxic formaldehyde on degradation in the body. Furthermore, microparticulate carriers are not suited for intravenous administration due to their size in the micrometer range.

Drug carrier systems for parenteral administration which are based on lipids are liposomes submicron o/w emulsions and lipid suspensions. These systems consist of physiological components only thus reducing toxicological problems associated with the carrier.

Liposomes are spherical colloidal structures in which an internal aqueous phase is surrounded by one or more phospholipid bilayers. The potential use of liposomes as drug delivery systems has been disclosed inter alia in the U.S. Pat. Nos. 3,993,754 (issued Nov. 23, 1976 to Rahmann and Cerny), 4,235,871 (issued on Nov. 25, 1980 to Papahadjopoulos and Szoka), and 4,356,167 (issued Oct. 26, 1982 to L. Kelly). The major drawbacks of conventional liposomes are their instability on storage, the low reproducibility of manufacture, the low entrapment efficiency and the leakage of drugs.

Lipid emulsions for parenteral nutrition are oil-in-water (o/w) emulsions of submicron-sized droplets of vegetable oils such as soya oil or of medium chain triglycerides dispersed in an aqueous medium. The liquid oil droplets are stabilized by an interfacial film of emulsifiers, predominantly phospholipids. Typical formulations are disclosed in the Jap. Pat. No. 55,476/79 issued on May 7, 1979 to Okamota, Tsuda and Yokoyama. The preparation of a drug containing lipid emulsion is described in WO 91/02517 issued on Mar. 7, 1991 to Davis and Washington. Due to the high diffusivity of incorporated drugs in the oil phase, the drug is released relatively fast from the emulsion vehicle upon administration into the blood stream. The oil is degraded to untoxic metabolites by the body within several hours. There is, however, a certain susceptibility of these lipid emulsions towards the incorporation of drugs due to the mobility of drug molecules within the internal oil phase since diffusing molecules can protrude into the emulsifier film. This might cause instabilities which lead to coalescence. Moreover, the solubility of poorly water soluble drugs in vegetable oils is often also relatively low. These carrier systems can therefore be used as a drug delivery system only in a very limited number of cases.

There are a number of micro- and nanoparticulate carrier systems which can be characterized as lipid suspensions. In these carrier systems a solid lipid phase is dispersed as micro- or nanoparticles in an aqueous medium. So-called lipospheres disclosed by Domb and Maniar (U.S. Pat. No. 435,546 lodged Nov. 13, 1989; Int. Appl. No. PCT/US90/06519 filed Nov. 8, 1990) are described as suspensions of solid, water-insoluble microspheres formed of a solid hydrophobic core surrounded by a phospholipid layer. Lipospheres are claimed to provide for the sustained release of entrapped substances which is controlled by the phospholipid layer. They can be prepared by a melt or by a solvent technique, the latter creating toxicological problems in case the solvent is not completely removed.

A slow release composition of fat or wax and a biologically active protein, peptide or polypeptide suitable for parenteral administration to animals is disclosed in U.S. Pat. No. 895,608 lodged Aug. 11, 1986 to Staber, Fishbein and Cady (EP-A-0 257 368). The systems are prepared by spray drying and consist of spherical particles in the micrometer size range up to 1,000 microns so that intravenous administration is not possible. The latter also applies to wax microparticles described by Bodmeier et al. (Bodmeier R., Wang J., Bhagwatwar, J. Microencapsulation 9 (1992) 89–98), or to ibuprofen containing microspheres of cetostearic alcohol reported by Wong et al. (Won, L. P., Gilligan C. A., Li Wan Po A., lnt. J. Pharm. 83 (1992) 95–114). Both systems can be prepared by crude dispersion of the molten lipid using a high speed stirrer.

In an attempt to improve the intestinal absorption of lipophilic drugs, Eldem et al. (Eldem T., Speiser P., Hincal A., Pharm. Res. 8 (1991) 47–54) prepared lipid micropellets by spray-drying and spray-congealing processes. The micropellets are described as solid. spherical particles with smooth surfaces. The lipids are present in the crystalline state. Due to the particle size in the micrometer range these micropellets cannot be used for intravenous administration.

Lipid pellets in the nanometer size range for peroral administration of poorly bioavailable drugs are disclosed in EP 0 167 825 issued Aug. 8, 1990 to P. Speiser. The nanopellets represent drug loaded fat particles solid at room temperature which are small enough to be persorbed. Persorption is the transport of intact particles through the intestinal mucosa into the lymph and blood compartment. Solid lipid nanospheres for parenteral administration are disclosed by Müller and Lucks in DE 41 31 562. These solid lipid nanospheres have been reported to be crystalline (Weyhers H., Mehnert W., Müller R. H., Europ. J. Pharm. Biopharm. 40 Suppl. (1994) 15S). The crystalline state of lipid nanoparticles described by Westesen et al. could be demonstrated by X-ray measurements (Westesen K., Siekmann B., Koch M. H. J., Int. J. Pharm. 93 (193) 189–199). All these systems represent carrier systems. The matrix materials of these carrier particles are exclusively composed of non-bioactive, pharmaceutically inert lipids.

Beside applicability by the parenteral route, particle size is also an important parameter governing the activity of the reticuloendothelial system (RES). Upon intravenous administration colloidal particles are in general rapidly removed from the blood stream by cells of the RES such as phagocytic macrophages. The rate of blood clearance by the RES depends inter alia on the size of the colloidal particles. Larger particles are generally cleared more rapidly than smaller ones so that the latter have a longer circulation time in blood and thereby a higher probability of the incorporated drug to reach its target site.

A colloidal particle can leave the blood by basically two different ways. On the one hand, this is possible by (receptor-mediated) uptake into cells by way of phagocytosis or pinocytosis. These processes are similar to the uptake by RES macrophages. On the other, the particles can leave the vascular system by so-called fenestrations of the endothelial wall. These fenestrations can be found e.g. in liver, spleen and bone marrow, but also at sites of inflammation or in tumour tissues. The diameters of these fenestrac are up to 150 nm. Extravasation through these fenestrations is of importance with respect to drug targeting to extravascular sites.

Beside the particle size effect, the rate of RES uptake is inter alia governed by the surface characteristics of the colloidal particles such as surface charge and surface hydrophilicity. It is generally accepted that colloidal particles should he uncharged and hydrophilic in order to avoid RES uptake. Thus there is a possibility to divert colloidal particles away from the RES by modifying their surface characteristics, e.g. by coating with polymers (Tröster S. D., Müller U., Kreuter J., Int. J. Pharm. 61 (1990) 85).

Surface properties play also an important role with regard to the dissolution process, e.g. in the GIT after peroral administration of poorly water soluble substances, and are therefore related to the bioavailability. Since apolar surfaces are only poorly wetted in aqueous media, another approach to increase the dissolution rate of sparingly water-soluble substances is thus hydrophilization of particle surfaces. From the field of pharmaceutical technology it is known that suitable surfactants are added to milled. hydrophobic powders as wetting agents in order to increase the wettability. Hydrophilization of apolar surfaces of poorly water-soluble bioactive agents can be obtained inter alia by processing these substances with water-soluble additives such as polyvinylpyrrolidone or polyethyleneglycol into spray-embeddings or co-precipitates.

Apart from reduction of particle size and improvement of wettability, the peroral bioavailability of a poorly water-soluble drug can be enhanced if the drug is not present in a crystalline but in an amorphous physical state. In general, amorphous forms of a substance exhibit a higher solubility and a faster dissolution than their crystal forms since the dissolution of amorphous substances does not require lattice energy. It is known, for example, that the antibiotic agent novobiocin can only be absorbed from the intestinum after administration of the amorphous substance which has a solubility ten times higher than the crystalline agent (Mullins J. D., Macek T. J., J. Am. Pharm. Assoc., Sci. Ed. 49 (1960) 245).

Ubidecarenone (6-Decaprenyl-2,3-dimethoxy-5-methyl-1,4-benzoquinone: coenzyme $Q_{10}$) is an endogenous quinone. In the human body it is localized in mitochondrial membranes and is involved in electron transport in the respiratory chain. The reduced form of the molecule is an antioxidant. Ubidecarenone is therapeutically used inter alia in cardiomyopathia, coronary diseases and for the prophylaxis of heart attack (Folkers K., Lituuru G. P., Yamagami T., (Eds.), Biomedical and Clinical Aspects of Coenzyme Q. Vol. 6. Elsevier 1991). Due to its general cell protective and energetic properties the substance is also applied as nutrient supplement for daily preventive intake.

Ubidecarenone is crystalline at room temperature and has a melting point of 49° C. (Rainasarma T., Adv. Lipid Res. 6 (1968) 107). The substance is commercially available as an orange-coloured powder consisting of crystal agglomerates in the micrometer to millimeter size range. Due to its long isoprenoid side chain the molecule is extremely lipophilic and practically insoluble in water.

The bloavailability of ubidecarenone is generally low due to the poor solubility in gastrointestinal fluids causing a low gastrointestinal absorption of the substance. Kishi et al. (in Folkers K., Yamamura Y., (Eds.). Biomediacal and Clinical Aspects of Coenzyme Q, Vol. 4, Elsevier 1984, pp. 131–142) observed that the peroral bioavailability of ubidlecarenone from solid dosage forms such as tablets and granules is related to the dissolution rate of the preparations. Kanamori et al. (Yakuzaigaku 45 (1985) 119–126) also report that the bioavailability of perorally administered ubidecarenone depends on the dosage form and decreases in the order soft gelatin capsule, granules and tablets.

A number of different formulations with the object to enhance the bioavailability of ubidecarenone can be found in the patent literature. Taki and Takahira disclose in EP 23349 (04.02.81) that the lymphatic absorption of orally administered ubidecarenone is increased by coadministration of long-chain fatty acids and monoglycerides. Increase of intestinal absorption by administration of capsules containing oily (surfactant) solutions of ubidecarenone is disclosed in different patents such as WO 8604503 A1 (14.08.86), JP 63188623 A2 (04.08.88), JP 62067019 A2 (26.03.87), JP 59148735 A2 (25.08.84) and JP 56012309 (06.02.81). Solubilization of ubidecarenone in micellar solutions is described in EP 522433 A1 (13.01.93), WO 8803019 A1 (05.05.88) and JP 59148718 A2 (25.08.84). Ueno et al. (Acta Pharm. Nord., 1 (1989) 99–104) report on the increase of peroral bioavailability by inclusion of ubidecarenone in a complex with β-cyclodextrins. A similar formulation is disclosed in JP 56109590 A2 (31.08.81). Moreover, incorporation of ubidecarenone in emulsions is reported to enhance intestinal absorption as described, for example, by Yano et al. in EP 494654 A2 (15.07.92).

For parenteral, in particular intravenous administration ubidecarenone has to be incorporated into a carrier vehicle since it is not possible to manufacture an aqueous solution with therapeutic concentrations of ubidecarenone due to its lipophilicity. Lecithin stabilized soya oil emulsions for intravenous administration of ubidecarenone are disclosed by Groke and Polzer (DE 3524788 A1, 22.01.87). Sugio et al. (JP 62123113 A2. 04.06.87) as well as Mizushima et al. (JP 60199814 A2. 09.10.85). JP 63319046 A2 (27.12.88) describes a soya oil emulsion vehicle coated by polysaccharides. The concentrations of ubidecarenone which can be incorporated in emulsions are, however, limited due to the relatively poor solubility of ubidecarenone in vegetable oils.

Liposome preparations of egg lecithin and cholesterol containing ubidecarenone are disclosed in EP 69399 A2 (12.01.83). Polysaccharide-modified liposomes are described e.g. in EP 94692 A1 (23.11.83). JP 60001124 A2 (07.01.85) and JP 63313727 A2 (21.12.88).

However, the disadvantage of incorporating a drug into a carrier system might be that an undesired change in the pharmacokinetics of the substance will be caused because the biodistribution is influenced by the biodistribution of the carrier, its RES activity and drug release from the carrier vehicle. Bogentoft et al. (in Folkers K., Littaru G. P., Yamagami T., (Eds.), Biomedical and Clinical Aspects of Coenzyme Q. Vol. 6. Elsevier 1991, pp. 215–224) observed that ubidecarenone accumulates in the RES organs when administered intravenously in a mixed micellar system or an emulsion vehicle, respectively. Furthermore, the solubility of the bioactive substance in the carrier is often too low to obtain therapeutic doses in acceptable volumes of the formulation. In addition, toxic side effects of the carrier particles by themselves have been discussed in the literature inter alia for parenteral lipid emulsions (Hajri T. et al., Biochim. Biophys. Acta 1047 (1990) 121–130; Connelly P. W. et al.; Biochim. Biophys. Acta 666 (1981) 80–89; Aviram M. et al., Biochem. Biophys. Res. Commun. 155 (1988) 709–713; Singh M. et al.; J. Parenter. Sci. Technol. 40 (1986) 34–40; Cotter R. et al., Am J. Clin. Nutr. 41 (1985) 994–1001; Untracht S., Biochim. Biophys. Acta711 (1982) 176–192).

From what is outlined above it is evident that ubidecarenone is a problematic substance with regard to pharmaceutical formulations of this drug. There are, however, by far more sparingly water soluble substances with similar formulation problems. The peroral bioavailability of these substances is poor due to the low aqueous solubility, and the intravenous administration is also problematic due to the lack of suitable intravenous formulations.

OBJECT OF THE INVENTION

The present invention introduces a novel and improved administration system for sparingly water-soluble and poorly wettable bioactive substances, in particular for ubidecarenone, based on dispersions or redispersible preparations of micron and, preferably, submicron-sized (colloidal) particles of poorly water-soluble substances which are solid, in particular crystalline, at room temperature in the bulk phase characterized in that the dispersed substance is primarily present in an amorphous physical state, in particular a liquid one, e.g. a supercooled melt. This administration system which is referred to as particles of supercooled melt (PSMs) has several advantages over conventional formulations which arise inter alia from the modified physical state of the substance in the (colloidal) particles, and provides for an improved bioavailability as well as for the direct parenteral, in particular intravenous administration of poorly water-soluble bioactive substances. PSMs can also be employed as a carrier system for poorly water-soluble bioactive agents, in particular for parenteral administration. Moreover, the invention also relates to a method to prepare this novel administration system characterized in that the process avoids the use of toxicological additives such as organic sovents, e.g. chlorinated hydrocarbons, and yields a product which is easy to handle from the security point of view since it is present as a dispersion in a pharmaceutically acceptable liqiud, preferably aqueous media.

DESCRIPTION OF THE INVENTION

The present invention relates to (colloidal) PSMs and their dispersions in pharmaceutically acceptable liquids, to a method for the manufacture thereof as well as to their use as an administration system for poorly water-soluble bioactive agents.

PSMs are (colloidal) particles of poorly water-soluble substances, optionally containing additives, finely dispersed in pharmaceutically acceptable liquids, preferably aqueous media, characterized in that the poorly water-soluble substance, e.g. ubidecarenone, which is solid and primarily crystalline at room temperature in the bulk phase (also referred to as bulk material), is present in a modified physical state in the PSMs and exists, completely or partly, in an amorphous, preferably liquid state, e.g. as a supercooled melt, at a temperature below the melting point of the bulk material, or at room temperature, i.e. approximately 20–25° C., or at body temperature, i.e. approximately 35–40° C. The solid bulk material (synonymously termed raw material or starting material) which is used as a starting material for preparing particles according to the present invention can be non-particulate or particulate, e.g. a powder, a precipitate, agglomerates, crystals or any other solid raw material commonly used.

An organic substance which is in the solid physical state at room temperature is generally called a solid. At temperatures below their melting point, crystalline solids form a crystal lattice which is characterized by a three-dimensional order of atoms or molecules. The term "supercooling" which is synonymously called "undercooling" means that a solid, crystalline substance is not present in a solid, crystalline state at temperatures below its bulk melting point, but in a melt- or liquid-like state which is characterized by a more random distribution of atoms or molecules such as in liquids. A supercooled or undercooled melt thus corresponds to an amorphous state which represents an amorphous liquid. However, the modified physical state of PSMs might alternatively represent an amorphous but solid state such as the vitreous or glassy state. Since these amorphous physical states are not ordered contrary to the crystalline state, dissolution of amorphous substances does not require crystal lattice energy. Amorphous substances therefore Generally display a higher solubility than their crystalline forms.

By the present invention it is possible to transform crystalline substances into an amorphous physical state, preferably into a supercooled melt. The amorphous state can be maintained in the particles of the present invention over a considerable time span which permits their use e.g. as a pharmaceutical drug administration or delivery system.

The PSMs of the present invention typically have particle size distributions in the low micrometer and in the nanometer size range with mean particle diameters determined by photon correlation spectroscopy (PCS) ranging predominantly from 30 to 500 nm. The particle core of PSMs consists of one or more poorly water-soluble substances which are primarily present in an amorphous, non-crystalline state, preferably as a supercooled melt.

In EP 0 002 425 Broberg and Evers disclose a preparation characterized in that by mixing of local anaestetics which have a melting point above room temperature, a homogenous oil is formed, i.e. an amorphous liquid state. This liquid state represents a cutectic. The state of a supercooled melt can, however, be clearly differentiated from a eutectic. Whereas a supercooled melt can be formed by a pure substance, the formation of a eutectic requires a mixture of at least two components. Moreover, these components must be present in a certain, clearly defined weight ratio to form a eutectic mixture. The eutectic mixture melts at a temperature below the melting points of each single component which is defined as the eutectic temperature. Below the eutectic temperature the mixture crystallizes. A eutectic mixture can form a supercooled melt in case that there is no crystallization of the eutectic mixture below the eutectic temperature. This state can then be characterized as the supercooled melt of a eutectic.

The characteristic state of a supercooled melt also distinguishes the particles of the present invention from conventional disperse systems for pharmaceutical use. In oil-inwater lipid emulsions which are used for parenteral nutrition and as intravenous drug carrier systems (Collins-Gold L. C., Lyons R. T., Bartholow L. C., Adv. Drug Deliv. Rev. 5 (1990) 189–208) the dispersed phase represents a pharmacologically acceptable oil and is thus liquid. The physical state of the dispersed phase corresponds to that of the bulk phase at a given temperature, e.g. room temperature, and therefore represents the thermodynamically stable state. The same applies principally to the above mentioned lipid suspensions such as solid lipid nanoparticles described by Westesen et al. (Westesen K., Siekmann B., Koch M. H. J., Int. J. Pharm. 93 (1993) 189–199), the difference to lipid emulsions being that the dispersed phase of the lipid suspensions is in a solid, crystalline state corresponding to that of the bulk material at room temperature. In the particles disclosed by Landh and Larsson in WO 93/06921 (15.04.93), the interior phase of the particles is constituted by a non-lamellar liquid-crystalline phase, and the particles are prepared by dispersion of non-lamellar lyotropic liquid-crystalline bulk phases by means of a fragmentation agent. The physical state of the dispersed particles thus corresponds to that of the bulk phase, i.e. a liquid-crystalline phase which is characterized by at least one-dimensional order of molecules or molecular aggregates, i.e. a non-amorphous state. In all these cases mentioned here the physical state of the dispersed phase is similar to that of the bulk material from which the particles are prepared. In contrast, the physical state of substances forming PSMs, which represents a supercooled melt, is modified compared to that of the substance in bulk and is thus different from that of the bulk material.

In case that stabilizing agents such as emulsifiers are used for the preparation of PSM dispersions, the PSM particle core is surrounded by one or more layers of stabilizing agents. Typically, amphiphilic substances, i.e. those with a hydrophilic and a hydrophobic part of the molecules, are employed as stabilizing agents.

At the PSM surface the amphiphilic substances are predominantly arranged in such a way that the hydrophobic part of the molecule protrudes into the particle core and the hydrophilic part into the surrounding dispersion medium. The surfaces of PSMs are therefore hydrophilic. The surface characteristics of PSMs can be modified, for example by the choice of stabilizing agents, or by the adsorption of polymers. Optionally, poorly water-soluble bioactive substances can he incorporated into PSMs. PSMs can be used as delivery or carrier systems primarily for the parenteral but also for the enteral, peroral, oral, mucosal, nasal, pulmonary, rectal, (trans)dermal and buccal administration of poorly water-soluble substances such as drugs or other biologically active materials from which they are prepared or which are incorporated in PSMs, respectively. The application of PSMs is, however, not restricted to the administration of pharmaceuticals to humans or animals. PSMs can also be used in cosmetic, food and agricultural products.

Dispersions of PSMs can be manufactured by a specific melt emulsification method which is characterized by the following steps:

1. The poorly water-soluble substance, e.g. ubidecarenone, or a mixture of poorly water-soluble substances is melted. Optionally, one or more additives which decrease the melting point of the poorly water-soluble substance(s) and/or impede or inhibit the recrystallization of the molten poorly water-soluble substance(s) can be added to the poorly water-soluble substance or mixture of poorly water-soluble substances.

2. Optionally, one or more stabilizing agents (e.g. amphiphilic substances, surfactants, emulsifiers) are dissolved or dispersed in the melt or in the dispersion medium depending on their physicochemical characteristics. Stabilizers can also be added or exchanged after homogenization, e.g. by adsorption of polymers or by dialysis of water-soluble stabilizers.

3. Preferably, the dispersion medium is heated to approximately the temperature of the melt prior to mixing and may contain e.g. stabilizers, isotonicity agents, buffering agents, cryoprotectants and/or preservatives.

4. Optionally, the dispersion medium and the melt are added and predispersed to give a crude dispersion, for example by shaking, stirring, sonication or vortexing. Predispersing is preferably carried out at temperatures above the melting point of the substance or the mixture of substances or the mixture of substances and additives, e.g. stabilizers, respectively. Predispersing can he omitted for well dispersible systems.

5. The (predispersed) melt is emulsified in the dispersion medium, preferably at temperatures above the melting point of the substance or the mixture of substances or the mixture of substances and additives, e.g,. stabilizers, respectively. Emulsification is preferably carried out by high pressure homogenization or by sonication, but may be also possible by high speed stirring, vortexing and vigorous hand shaking. The way of homogenization determines the particle size distribution and the mean particle size of PSMs.

6. Bioactive agents which are to be incorporated into PSMs such as lipophilic drugs can be melted together with the poorly-water soluble substance(s) constituting the particles; be dissolved, solubilized or dispersed in the melt prior to emulsification; be incorporated in PSMs after homogenization, e.g. by sonication; or be adsorbed to the surface of the particles. The way of incorporation depends on the physicochemical properties of the bioactive agents to be incorporated.

After preparation the fine dispersions of PSMs can be further processed, for example by (sterile) filtration, ultrafiltration, dialysis, surface modification (e.g. by adsorption of polymers), sterilization or lyophilization. PSMs can also be processed into other dosage fonris. For example, PSM dispersions can be processed into hydrogels for topical application by addition of a gel forming agent to the aqueous phase.

PSMs of ubidecarenone manufactured according to the procedure described above represent predominantly spherical particles of submicron size and which are predominantly present in an amorphous state at room temperature, more specifically as a supercooled melt, i.e. as a liquid. Ubidecarenone-PSMs consist of an amorphous, predominantly liquid core of ubidecarenone which is covered by one or more layers of preferably physiological or toxicologically inert stabilizers. By a proper choice of stabilizing agents the particle surface properties can be modified. Ubidecarenone-PSMs can be distinguished from conventional formulations of ubidecarenone by their modified physicochemical properties such as their structure (liquid physical state of a supercooled melt), their physicochemical properties (e.g. modified surface characteristics) and their particle size (nanometer size range). Ubidecarenone-PSMs can be applied for the enteral, parenteral and topical administration of ubidecarenone as well as of other substances which can be incorporated into ubidecarenone-2 PSMs. The release of incorporated drugs can be controlled to a certain extent by the choice of stabilizing agents surrounding the particle core. Compared to drug carrier vehicles based on lipid emulsions, ubidecarenone-PSMs have the advantage that they are less rapidly degraded in the blood than triglycerides of lipid emulsions. Thus drug release can be sustained. Since ubidecarenone is nontoxic, ubidecarenone-PSMs can be applied in high doses. Moreover, disadvantages of carrier systems (e.g. lipid emulsions, lipid suspensions, dispersions of liquid crystalline phases) such as low drug pay load of the carrier or side effects caused by the carrier particles themselves can be circumvented by the use of PSMs.

It can be theoretically deduced that PSMs analogous to those of ubidecarenone can principally be prepared from other substances as well, and this has been confirmed experimentally as described in the Examples listed below. Substances which are particularly suited for the preparation of aqueous PSM dispersions are characterized by a poor solubility in aqueous media. They have a melting point preferably below approximately 100–130° C. or their melting point can be decreased to below 100–130° C. by the addition of additives which decrease the melting point, and/or their recrystallization from the melt is impaired or inhibited or can be impaired or inhibited by the addition of additives. Substances with these properties can be bioactive agents which exhibit a poor bioavailability after peroral administration due to their low solubility in Gastrointestinal fluids, or the formulation of which as a parenteral dosage form is problematic; or pharmacologically acceptable substances which are suited as carrier materials for poorly water-soluble drugs or other bioactive agents; or bioactive agents the industrial processing and handling of which shall be improved. Suitable substances with these properties can be found in the Examples listed below. The physicochemical properties of the substance which determine the properties of the fine dispersed material, that means if the dispersed substance exists in an amorphous, preferably liquid, i.e. supercooled state over a longer period of time, or transforms into a solid crystalline state, are given by the Thomson equation via the ratio of the melting point T of small particles of radius r and the normal melting point $T_O$ of the bulk material $$\ln (T/T_O) = (2\gamma_{SL} \cdot V_S)/(r\Delta H_{fus}),$$

and comprise the surface tension of the solid $\gamma_{SL}$, the molar volume of the solid $V_S$, the particle/grain size, and the heat of fusion $\Delta H_{fus}$ (Hunter R. J. (1986) "Foundations of Colloid Science", Vol. 1, Oxford University Press, Oxford, p. 268). They are thus inter alia related to the complexity of the crystal lattice of the bulk material. With respect to the size dependence of the physical state of the dispersed particles, a smaller particle size generally favours the liquid state of a supercooled melt. The critical size below which a substance is predominantly present in an amorphous liquid state is, however, different for different substances and depends also on other physicochemical properties of the substances, e.g. such as listed above, in particular on the crystallization tendency of the substance. Furthermore the physical state of dispersed particles can be influenced by the presence of surface active stabilizing agents, and might also be influenced by the temperature treatment after dispersion of the molten substance. It is therefore possible that particles with different properties concerning their physical state might be obtained by basically the same manufacturing process depending on the physicochemical properties of the bulk material which is dispersed, as well as on the process parameters such as e.g. homogenization time and homogenization pressure since the latter influence the size of the dispersed particles. Thus particles with a solid interior phase, e.g. lipid suspensions described by Domb and Maniar in U.S. Pat. No. 435,546 or by Westesen et al. (Westesen K., Siekmann B., Koch M. H. J., Int. J. Pharm. 93 (1993) 189–199). can also be prepared by a melt emulsification process. The product of the process is, however, different from PSMs with respect to the physical state of the dispersed phase. In the dispersion process disclosed by Domb and Maniar in U.S. Pat. No. 435,546 the molten and dispersed particles are forced into the solid state by a temperature treatment, e.g. fast cooling after emulsification. During the production of solid lipid nanoparicles by melt emulsification according to Westesen et al. (Westesen K., Siekmann B., Koch M. H. J., Int. J. Pharm. 93 (1993) 189–199), the metastable state of a supercooled melt of the lipids might be passed temporarily, but due to the physicochemical properties of the lipids employed for the preparation of solid lipid nanoparticles, such as e.g. the high crystallization tendency, these lipids recrystallize within a relatively short period alter production to form solid particles.

Dispersions of PSMs can be stabilized by amphiphatic compounds such as ionic and non-ionic surfactants. Suitable stabilizers include but are not limited to the following examples: naturally occuring as well as synthetic phospholipids, their hydrogenated derivatives and mixtures thereof; sphingolipids and glycosphingolipids; physiological bile salts such as sodium cholate, sodium dehydrocholate, sodium deoxycholate, sodium glycocholate and sodium taurocholate; saturated and unsaturated fatty acids or fatty alcohols; ethoxylated fatty acids or fatty alcohols and their esters and ethers; alkylaryl-polyether alcohols such as tyloxapol; esters and ethers of sugars or sugar alcohols with fatty acids or fatty alcohols; acetylated or ethoxylated mono- and diglycerides; synthetic biodegradable polymers like block co-polymers of polyoxyethylene and polyoxypropyleneoxide; ethoxylated sorbitanesters or sorbitanethers; amino acids, polypeptides and proteins such as gelatine and albumin; or a combination of two or more of the above mentioned.

In contrast to the preparation of stable dispersions of solid lipid nanoparticles, the choice of stabilizers for the preparation of stable dispersions of PSMs is less critical since PSMs do not recrystallize. Recrystallization of the dispersed substances might result in the destabilization of the dispersed state and in formation of gel-like networks of resolidified material, which can, however, be circumvented by a proper choice of emulsifiers (Westesen K., Siekmann B., Eur. J. Pharm. Biopharm. 40 Suppl. (1994) 35S). In contrast, the criteria for the emulsifier choice in the case of PSMs is comparable to that for the stabilization of conventional pharmaceutical submicron-sized oil-in-water emulsions. Emulsifiers approved for parenteral emulsions have been toxicologically evaluated for several decades and are considered to be pharmaceutically acceptable even with respect to administration of large volumes, e.g. for parenteral nutrition.

The dispersion medium, preferably aqueous phases, in which PSMs are dispersed can contain water soluble or dispersible stabilizers; isotonicity agents such as glycerol or xylitol; cryoprotectants such as sucrose, glucose, trehalose etc.; electrolytes; buffers; antillocculants such as sodium citrate, sodium pyrophosphate or sodium dodecylsulfate; preservatives.

Depending on the characteristics of the employed stabilizers, the coexistence of other colloidal structures such as micelles and vesicles in dispersions of PSMs cannot be ruled out.

Substances particularly suitable for the entrapment into PSMs are drugs or other bioactive compounds which are poorly water-soluble, show a low bioavailability, are badly absorbed from the intestinum, as well as low-specific active substances which are highly toxic at non-target sites. In case it is desired to incorporate a relatively water soluble compound into PSMs, it might be necessary to decrease the solubility of this compound in the dispersion medium which can be achieved, for example, by using a water insoluble derivative of the compound such as an acid or base, a complex, or a lipophilic precursor.

Drugs or bioactive agents which are particularly suited for incorporation into PSMs are anesthetics such as butanilicain, fomocain, lidocain, prilocain, tetracain und etomidate; antibiotics such as fosfomycin, fosmidomycin and rifapentin; antihypertensives such as minoxidil, dihydroergotoxine and endralazine; antihypotensives such as dihydroergotamine; systemic antimycotics such as ketoconazole, miconazole and griseofulvin; antiphiogistics such as indomethacin, diclofenac, ibuprofen, ketoprofen and pirprofen; antiviral agents such as aciclovir, vidarabin and immunoglobulines; ACE inhibitors such as captopril and enalapril; betablockers such as propranolol, atenolol, metoprolol, pindolol, oxprenolol and labetalol; bronchodilators such as ipratropiumbromide and sobrerol; calcium antagonists such as diltiazem, flunarizin, verapamil, nifedipin, nimodipin and nitrendipin; cardiac glycosides such as digitoxin, digoxin, methyldigoxin and acetyldigoxin; cephalosporins such as ceftizoxim, cefalexin, cefalotin and cefotaxim; cytostatics such as chlormethin, cyclophosphamid, chlorambucil, cytarabin, vincristin, mitomycin C, doxorubicin, bleomycin, cisplatin, taxol, penclomedine and estramustin; hypnotics such as flurazepam, nitrazepam and lorazepam; psychotropic drugs such as oxazepam, diazepam and bromazepam; steroid hormones such as cortisone, hydrocortisone, prednisone, prednisolone, dexamethasone, progesterone, pregnanolone, testosterone and testosterone undecanoate; vasodilators such as molsidomin, hydralazin and dihydralazin; cerebral vasodilators such as dihydroergotoxin, ciclonicat and vincamin; ubiquinones and their analogues such as ubidecarenone and atovaquon; lipophilic vitamins such as vitamin A, E, D, K and their derivates; insecticides, herbicides and pesticides such as acephate, cyfluthrin, azinphosphomethyl, cypermethrin, fenclofos, permelthrin, piperonal, tetramethrin and trifluralin.

The bioactive substances can be located in the core of PSMs where they are dissolved, solubilized or dispersed in the matrix, and/or in the stabilizer layer(s) surrounding the particle core, and/or can be adsorbed to the surface of PSMs. The bioactive substances can be dissolved or crystalline or amorphous or a mixture of these crystallographic states.

The advantages of aqueous PSM dispersions over conventional formulations for the administration of poorly water-soluble drugs can bc deduced from the characteristics of PSMs as described above, in particular from the combination of the amorphous state of the particles at body and room temperature, their small particle size and their hydrophilized surfaces. The present invention is therefore supposed to bring about the following advantages:

1. Since the bioactive substance formulated as PSMs is completely or partly present in an amorphous physical state, preferably in the liquid state, e.g. a supercooled melt, dissolution of the substance does not require or, respectively, requires less energy than the crystalline substance which needs to overcome lattice forces. The dissolution rate of PSMs is therefore increased as well as its solubility resulting in an enhanced bioavailability compared to the crystalline bulk substance.
2 Disadvantages of carrier systems for bioactive substances such as low pay load of the carrier or toxicological side effects which are related to the carrier particles themselves can be circumvented by the use of PSMs.
3. The .small particle size of PSMs in the nanometer size range can generally not be achieved by conventional comminution techniques such as milling, grinding or micronization. The small particle size results in a tremendous increase of the specific surface area compared to conventional administration systems such as (micronized) powders or granulates. Since the solubility is related to particle size via the dissolution rate, size reduction results in an increased dissolution rate. It is well known that the peroral bioavailability of bioactive agents depends on their dissolution rate in gastrointestinal fluids. Consequently, the bioavailability of bioactive agents formulated as colloidal PSMs can be improved.
4. Formulation of PSMs according to the present invention with particle sizes in the nanometer size range renders possible the direct parenteral administration of practically water-insoluble substances. Due to the small particle size of PSMs, dispersions thereof can be administered intravenously without risk of embolism which is not possible for the crystalline bulk substance suspended in an aqueous medium.
5. The achievable particle size of PSMs is below 150 nm which corresponds to the diameter of the fenestrations of the endothelial wall of blood vessels. Intravenously administered PSMs therefore have the potential to leave the vascular compartment via these fenestrations. Drugs formulated as PSMs or incorporated into PSMs can thus be transported within the particles to extravascular targets such as the bone marrow or tumor tissues.
6. Since PSMs are covered by stabilizing agents, they have hydrophilic surfaces and therefore exhibit a good wettability. A good wettability, e.g. in the gastrointestinal tract, facilitates the dissolution of the substance which leads to an improved bioavailability.
7. The surface characteristics of PSMs can be modified e.g. by the choice of stabilizing agents, by the adsorption of polymers or by the attachment of so-called homing-devices such as monoclonal antibodies or carbohydrate moieties. It is possible to modify the bloavailability and the biodistribution with respect to the rate and extent of absorption, the circulation time in the vascular compartment, the transport to the site of action and the organ distribution by modification of surface properties.
8. PSMs, in particular those formulated from pharmacologically inactive substances, can be used as (colloidal) carrier systems for poorly water-soluble, especially lipophilic bioactive agents such as drugs. Drug-loaded PSMs can be administered by enteral, parenteral, peroral, oral, mucosal, rectal, pulmonal, ophthalmic and (trans)dernal routes.
9. The process of manufacturing of PSMs involves unexpensive conventional techniques only and provides a product which is sale with respect to its handling. In contrast to the production of extremely fine powders there is no risk of dust explosions, cross-contamination in a factory environment or inhalation of bioactive substances by personnel since the particles are present in an aqueous dispersion. Moreover, the production method of PSMs does not involve toxicologically hazardous additives such as chlorinated hydrocarbons or other organic solvents, and can be accomplished with physiological additives only thereby circumventing problems of toxic residues.

EXAMPLES

Example 1:

3.0 g ubidecarenone is melted in a thermostatized vessel at 70° C. 1.8 g lecithin (Phospholipon 100. Nattermann) is dispersed in the melt by sonication (Soniprep, MSE). 95.2 g bidistilled water heated to 70° C. is added to the dispersion of lecithin in molten ubidecarenone. The warm mixture is predispersed by high speed vortexing (Ultra Turrax) for 120 sec. The predispersion is homogenized at 900 bar for 10 min in a high pressure homogenizer type Microfluidizer (Microfluidics Corp.) which is immersed in a water bath heated to 70° C. The dispersion is allowed to stand at room temperature for cooling.

The mean particle size (number distribution) of the dispersion is determined by photon correlation spectroscopy (PCS: Zetasizer 3, Malvern) to be 102.5 nm.

Example 2:

3.0 g ubidecarenone is melted in a thermostatized vessel at 70° C. 1.5 g lecithin (Phospholipon 100, Nattermann) is dispersed in the melt by sonication (Soniprep. MSE). 300 mg sodium glycocholate is dissolved in 95.2 g bidistilled water, and the solution is heated to 70° C. The heated aqueous phase is added to the dispersion of lecithin in molten ubidecarenone. The warm mixture is predispersed by high speed vortexing (Ultra Turrax) for 120 sec. The predispersion is homogenized at 900 bar for 10 min in a high pressure homogenizer type Microfluidizer (Microfluidics Corp.) which is immersed in a water bath heated to 70° C. The dispersion is allowed to stand at room temperature for cooling.

The mean particle size (number distribution) of the dispersion determined by PCS is 68.5 nm. Ubidecarenone nanoparticles display a narrow particle size distribution (FIG. 1). For comparison, FIG. 2 illustrates the particle size distribution of the powdered raw material of ubidecarenone used for preparation of the nanoparticles as determined by laser diffractometry (Mastersizer, Malvern). For the measurement the powder was dispersed in an aqueous solution of 0.3% sodium glycocholate. The particle size distribution of the powders ranges from the lower micrometer up to the millimeter size range. The complete distribution can, however, not be completely determined due to the limited measurement range of the instrument (up to 600 $\mu$m). The volume distribution mean with respect to the covered measurement range is 237.5 $\mu$m.

Example 3:

In order to estimate the stability on storage of the aqueous dispersions of ubidecarenone prepared according to Example 1 and 2, the particle size of the dispersions stored at 4° C. was repeatedly determined by PCS at different time intervals over a monitored period of 30 months. FIG. 3 presents the mean particle size of ubidecarenone nanoparticles of Example 1 and 2 versus storage time. The mean particle is practically constant over the monitored period of 30 months. Ubidecarenone nanoparticles thus exhibit an excellent stability on storage.

Example 4:

3.0 g ubidecarenone is melted in a thermostatized vessel at 70° C. 1.8 g lecithin (Phospholipon 100, Nattermann) is dispersed in the melt by sonication (Soniprep, MSE). 380 mg sodium glycocholate is dissolved in 94.8 g bidistilled water, and the solution is heated to 70° C. The heated aqueous phase is added to the dispersion of lecithin in molten ubidecarenone. The warm mixture is predispersed by high speed vortexing (Ultra Turrax) for 120 sec. The predispersion is homogenized at 900 bar for 10 min in a high pressure homogenizer type Microfluidizer (Microfluidics Corp.) which is immersed in a water bath heated to 70° C. The dispersion is allowed to stand at room temperature for cooling.

The mean particle size (number distribution) determined by PCS is 69.9 nm. FIG. 4 illustrates the time course of particle comminution by microfluidizer homogenization. During homogenization small sample volumes for size analysis were taken from the dispersion after each minute. The particle size of ubidecarenone particles is decreasing with homogenization time. The graph levels off asymptotically, i.e. when a certain size limit is reached the particle size cannot be further reduced by additional homogenization cycles.

FIG. 5 displays a transmission electron micrograph of a freeze-fractured replica of the ubidecarenone dispersion. Uhidecarenone nanoparticles are predominantly spherical. The amorphous particle core indicates the amorphous state of ubidecarenone which cannot be distinguished to he solid or liquid from this micrograph.

Example 5:

2.5 g ubidecarenone is melted in a thermostatized vessel at 70° C. 450 mg lecithin (Phospholipon 100, Nattermann) is dispersed in the melt by sonication (Soniprep. MSE). 210 mg sodium glycocholate is dissolved in 46.8 g bidistilled water, and the solution is heated to 70° C. The heated aqueous phase is added to the dispersion of lecithin in molten ubidecarenone. Probe sonication (Soniprep. MSE) for 120 min at 70° C. yields a fine dispersion of ubidecarenone nanoparticles. After cooling to room temperature evaporated water is substituted. The dispersion is centrifuged at 4000 rpm in a laboratory centrifuge for 20 min to remove metal shed of the sonication probe.

Determination to the size distribution by laser diffractometry (Mastersizer, Malvern) reveals that all particles of the ubidecarenone dispersion have a size below 0.83 $\mu$m (FIG. 6). After 3 years of storage the ubidecarenone nanoparticles have a mean PCS particle diameter of 172.6 nm.

Example 6:

4.0 g ubidecarenone is melted in a thermostatized vessel at 70° C. 2.4 g lecithin (Phospholipon 100, Nattermann) is dispersed in the melt by sonication (Soniprep, MSE). 500 mg sodium glycocholate is dissolved in 33.1 g bidistilled water, and the solution is heated to 70° C. The heated aqueous phase is added to the dispersion of lecithin in molten ubidecarenone. The warm mixture is predispersed by sonication (Soniprep, MSE) for 3 min. The predispersion is homogenized at 500 bar for 5 cycles in a high pressure homogenizer type Micron Lab 40 (APV Gaulin) which was heated to 80° C. The dispersion is allowed to stand at room temperature for cooling.

The mean particle size (number distribution) determined by PCS is 144 nm.

Example 7:

1.2 g ubidecarenone is melted in a thermostatized vessel at 70° C. 840 mg tyloxapol is dissolved in 38.0 g bidistilled water heated to 70° C. The heated aqueous phase is added to the melt of ubidecarenone. The warm mixture is predispersed by sonication (Soniprep, MSE) for 3 min. The predispersion is homogenized at 1200 bar for 10 cycles in a high pressure homogenizer type Micron Lab 40 (APV Gaulin) which was heated to 80° C. The dispersion is allowed to stand at room temperature for cooling.

The mean particle size (number distribution) determined by PCS is 67.3 nm.

Example 8:

To characterize the physical state of ubidecarenone nanoparticles, the dispersions of Examples 1, 2, 5, 6 and 7 are investigated by differential scanning calorimetry (DSC). Approximately 10 mg of each dispersion is accurately weighed on a micro-balance into standard aluminium pans (Perkin Elmer). The samples are measured in a DSC-2C calorimeter (Perkin Elmer) at a heating rate of 10° C./min from 20–70° C. using an empty aluminium pan as reference. A calibration curve is recorded under the same experimental conditions by recording the thermograms of different concentrations of crystalline ubidecarenone powder dispersed in water.

FIG. 8 displays the recorded DSC thermograms of the investigated ubidecarenone nanoparticles compared to a dispersion of 3% crystalline ubidecarenone. In contrast to crystalline ubidecarenone which exhibits a clear melting peak, ubidecarenone nanoparticles do not display any thermal transition over the investigated temperature range. These results indicate that ubidecarenone nanoparticles are in an amorphous liquid state.

Example 9:

A wide angle X-ray diffraction pattern of the aqueous ubidecarenone dispersion prepared according to Example 1 is recorded. The aqueous dispersion is filled into a sample cell thermostatized at 20° C. Due to the small particle size and the relatively low concentration of ubidecarenone in the dispersion it can be assumed that crystalline portions of the substance, which could be possibly present in the dispersions, cannot be detected by a conventional X-ray source. X-ray measurements were therefore performed by use of a synchrotron radiation source at the storage ring DORIS of the Deutsches Elektronen Synchrotron (DESY), Hamburg. Reflections were recorded in the observation range $1.7 < s < 2.8$ nm$^{-1}$ where $s = 2 \sin \Theta / \lambda$ with $2\Theta$ being the scattering angle and $\lambda$ the wavelength of radiation (0.15 nm).

FIG. 9 illustrates the wide angle X-ray diffraction patterns of the powdered raw material ubidecarenone (9.a) and the ubidecarenone dispersion of Example 1 (9.b). It can be observed that the dispersions does not display any detectable reflections, and it can thus be concluded that ubidecarenone in the aqueous dispersion is present in an X-ray amorphous state.

Example 10:

1.2 g ubidecarenone is melted in a thermostatized vessel at 70° C. 150 mg lecithin (Phospholipon 100, Nattermann) is dispersed in the melt by sonication (Soniprep, MSE). 50 mg sodium glycocholate is dissolved in 38.7 g deuterium oxide (deuterated water), and the solution is heated to 70° C. The heated aqueous phase is added to the dispersion of lecithin in molten ubidecarenone. Probe sonication (Soniprep, MSE) for 60 min at 70° C. yields a fine dispersion of ubidecarenone nanoparticles. The dispersion is allowed to stand at room temperature for cooling. The mean particle size (number distribution) determined by PCS is 141.3 nm.

For investigation of the physical state of ubidecarenone nanoparticles a proton resonance spectrum is recorded on a high resolution NMR spectrometer (Bruker). Under the chosen experimental conditions the instrument is a selective indicator of hydrogen nuclei in molecules which are in a liquid or dissolved state. The obtained $^1$H-NMR spectrum is presented in FIG. 10.c. For comparison the spectra of an aqueous solution of sodium glycocholate and of a suspension of crystalline ubidecarenone in sodium glycocholate solution prior to and after heating above the melting point of ubidecarenone were recorded. The suspension of ubidecarenone displays the typical resonances of ubidecarenone only in the molten state. The spectrum of the dispersion of crystalline ubidecarenone corresponds to that of the aqueous sodium glycocholate solution (FIG. 10.a). In contrast, the spectrum of ubidecarenone nanoparticles prepared in deuterated water (FIG. 10.c) corresponds to that of the molten ubidecarenone suspension (FIG. 10.b). It can thus be concluded that ubidecarenone nanoparticles are liquid.

Example 11:

160 mg sodium glycocholate is dissolved in 37.9 g bidistilled water. 720 mg lecithin (Lipoid S 100, Lipoid KG) is dispersed in the solution by magnetic stirring for several hours. 1.2 g ubidecarenone is melted in a thermrostatized vessel at 70° C. The aqueous phase is heated to 70° C., and is added to the melt of ubidecarenone. A predispersion is prepared by sonication which is homogenized for 10 cycles at 1200 bar in a high pressure homogenizer type Micron Lab 40 thermostatized at 80° C. The dispersion is allowed to stand at room temperature for cooling.

Example 12:

1.2 g ubidecarenone is melted in a thermostatized vessel at 70° C. 720 mg lecithin (Lipoid S 100, Lipoid KG) is dispersed in the melt by sonication (Soniprep, MSE). 40 mg retijiol (vitamin A) is dissolved in the melt 160 mg sodium glycocholate is dissolved in 37.9 g bidistilled water, and the solution is heated to 70° C. The heated aqueous phase is added to the retinol containing dispersion of lecithin in molten ubidecarenone. The warm mixture is predispersed by sonication (Soniprep, MSE) for 3 min. The predispersion is homogenized at 1200 bar for 10 cycles in a high pressure homogenizer type Micron Lab 40 (APV Gaulin) thermostatized at 80° C. The dispersion is allowed to stand at room temperature for cooling.

The mean particle size (number distribution) determined by PCS is 110.9 nm. Repeated DSC measurements according to the description in Example 8 at different time intervalls during storage of the sample in a refrigerator do not reveal any thermal transition.

Example 13:

1.2 g ubidecarenone is melted in a thermostatized vessel at 70° C. 720 mg lecithin (Lipoid S 100, Lipoid KG) is dispersed in the melt by sonication (Soniprep, MSE). 40 mg menadione (vitamin $K_3$) is dissolved in the melt. 160 mg sodium glycocholate is dissolved in 37.9 g bidistilled water, and the solution is heated to 70° C. The heated aqueous phase is added to the retinol containing dispersion of lecithin in molten ubidecarenone. The warm mixture is predispersed by sonication (Soniprep, MSE) for 3 min. The predispersion is homogenized at 1200 bar for 10 cycles in a high pressure homogenizer type Micron Lab 40 (APV Gaulin) thermostatized at 80° C. The dispersion is allowed to stand at room temperature for cooling.

The mean particle size (number distribution) determined by PCS is 102.0 nm. Repeated DSC measurements according to the description in Example 8 at different time intervalls during storage of the sample in a refrigerator do not reveal any thermal transition.

Example 14

1.0 colecalciferol is melted. 1.25 g glycerol (70%) and 4 mg thiomersal are dissolved in 37.5 g bidistilled water. 240 mg soya lecithin (Lipoid S 100, Lipoid KG) is dispersed in the aqueous solution by probe sonication (MSE Soniprep). 80 mg sodium glycocholate is dissolved in this dispersion. The aqueous phase is heated to 95° C. and is added to the melt of colecalciferol. The mixture is predispersed by probe sonication in a thermostatized vessel at 95° C. The predispersion is passed five times through a high pressure homogenizer (APV Gaulin Micron Lab 40) thermostatized at 95° C. The homogenization pressure is 800 bar. The dispersion of PSMs is allowed to stand at room temperature for cooling.

The mean particle size (number distribution) determined by PCS is 216.1 nm after preparation. The DSC thermogram of the PSM dispersion of colecalciferol does not reveal any transition peak in the temperature range from 20 to 95° C. pointing to the presence of amorphous particles of colecalciferol.

Example 15

800 mg colecalciferol is melted. 120 mg soya lecithin (Lipoid S 100, Lipoid KG) is dispersed in the melt by probe sonication (MSE Soniprep). 1.2 g glycerol (70%), 40 mg sodium glycocholate and 4 mg thiomersal are dissolved in 36.5 g bidistilled water. The aqueous phase is heated to 95° C. and is added to the melt. The mixture is predispersed by probe sonication in a thermostatized vessel at 95° C. The predispersion is passed five times through a high pressure homogenizer (APV Gaulin Micron Lab 40) thermostatized at 95° C. The homogenization pressure is 800 bar. The dispersion of PSMs is allowed to stand at room temperature for cooling. The mean particle size (number distribution) determined by PCS is 321 nm.

The physical state of the PSM dispersion of Example 15 is determined by DSC in the temperature range from 20 to 90° C. at a heating rate of 5° C./min. FIG. 11 represents the DSC thermogram of the dispersion after 14 months of storage at 4° C. compared to the thermogram of a suspension of 2% crystalline colecalciferol powder in water. Whereas the crystalline powder displays an endothermic peak around 77° C. corresponding to its melting, the thermogram of the PSM dispersion does not reveal any transition peak. This example demonstrates that the colloidal colecalciferol PSMs can he kept in the state of a supercooled melt, i.e. in an amorphous state, over an extended period of storage.

The synchrotron radiation small and wide angle X-ray diffraction pattern of the colecalcilerol particles does not display any spacings corresponding to crystalline colecalciferol and thus also points to the amorphous state of the colloidal particles of colefalciferol.

Example 16

2.0 g tocopherol acid succinate is melted. 1.2 glycerol (70%) and 4 mg thiomersal are dissolved in 36.5 g bidistilled water. 490 mg soya lecithin (Lipoid S 100, Lipoid KG) is dispersed in the aqueous solution by probe sonication (MSE Soniprep). 160 mg sodium glycholate is dissolved in this dispersion. The aqueous phase is heated to 90° C. and is added to the melt of tocopherol acid succinate. The mixture is predispersed by probe sonication in a thermostatized vessel at 90° C. The predispersion is passed five times through a high pressure homogenizer (APV Gaulin Micron Lab 40) thermostatized at 90° C. The homogenization pressure is 800 bar. The dispersion of PSMs is allowed to stand at room temperature for cooling.

The mean particle size by number after preparation is 188.7 nm determined by PCS.

The physical state of the PSM dispersion of Example 16 is determined by DSC in a temperature range from room temperature to approximately 10° C. above the melting point of the bulk substance at a scan rate of 5° C./min. The DSC thermogram of the tocopherol acid succinate particle dispersions does not reveal any thermal transition. From the absence of a transition peak it can be concluded that the colloidal particles of tocopherol acid succinate are not crystalline but amorphous. The absence of a second order phase transition (glas transition) hints at a liquid physical state of the dispersed particles of tocopherol acid succinate. In contrast, a suspension of 5% crystalline tocopherol acid succinate in water clearly reveals a melting peak at around 74° C.

Example 17

4.0 g cholesteryloleate is melted. 970 mg soya lecithin (Lipoid S 100, Lipoid KG) is dispersed in the melt by probe sonicalion (MSE Soniprep). 1.1 glycerol (70%), 240 mg sodium glycocholate and 4 mg thiomersal are dissolved in 34.8 g bidistilled water. The aqueous phase is heated to 60° C. and is added to the melt. The mixture is predispersed by probe sonication in a thermostatized vessel at 60° C. The predispersion is passed five times through a high pressure homogenizer (APV Gaulin Micron Lab 40) thermostatized at 80° C. The homogenization pressure is 800 bar. The dispersion of PSMs is allowed to stand at room temperature for cooling. The mean particle size by number after preparation is 176.4 nm determined by PCS.

The physical state of the PSM dispersion of Example 17 is determined by DSC in a temperature range from room temperature to approximately 10° C. above the melting point of the bulk substance at a scan rate of 5° C./min. The DSC thermogram of the cholesteryloleate dispersion does not reveal any transition peak pointing to the presence of amorphous particles of cholesterloleate. The absence of a second order phase transition (glas transition) hints at a liquid physical state of the dispersed particles of cholesterloyloleate. In contrast, a suspension of 10% crystalline cholesteryloleate in water clearly reveals a melting peak at around 40.5 ° C.

Example 18

4.0 g cholesteryloleate is melted and 200 mg of the heart protecting drug ubidecarenone is dissolved in the melt. 970 mg soya lecithin (Lipoid S 100, Lipoid KG) is dispersed in the melt by probe sonication (MSE Soniprep). 1.1 g glycerol (70%), 240 mg sodium glycocholate and 4 mg thiomersal are dissolved in 34.8 g bidistilled water. The aqueous phase is heated to 60° C. and is added to the melt. The mixture is predispersed by probe sonication in a thermostatized vessel at 60° C. The predispersion is passed five times through a high pressure homogenizer (APV Gaulin Micron Lab 40) thermostatized at 80° C. The homogenization pressure is 800 bar. The drug-loaded dispersion of PSMs is allowed to stand at room temperature for cooling. The particle size distribution is similar to that of Example 17.

Example 19

4.0 g trimyristate (Dynasan 114, Hüls AG, Witten) is melted. 640 mg soya lecithin (Lipoid S 100, Lipoid KG) is dispersed in the melt by probe sonication (MSE Soniprep). 1.0 g glycerol, 160 mg sodium glycocholate and 4 mg thiomersal are dissolved in 34.2 g bidistilled water. The aqueous phase is heated to 70° C. and is added to the melt. The mixture is predispersed by probe sonication in a thermostatized vessel at 70° C. The predispersion is passed five times through a high pressure homogenizer (APV Gaulin Micron Lab 40) thermostatized at 80° C. The homogenization pressure is 800 bar. The dispersion of PSMs is allowed to stand at room temperature for cooling. The mean particle size by number after preparation is 109.4 nm determined by PCS.

The physical state of the PSM dispersion of Example 19 is determined by DSC in a temperature range from 20 to 100° C. (FIG. 12a). The DSC thermogram of the dispersion does not reveal any transition peak pointing to the presence of amorphous particles. The absence of a second order phase transition (glas transition) hints at a liquid physical state of the dispersed particles.

Example 20

4.0 g Witepsol H42 (Hüls AG, Witten) is melted. 800 mg soya lecithin (Lipoid S 100, Lipoid KG) is dispersed in the melt by probe sonication (MSE Soniprep). 1.0 g glycerol, 800 mg tyloxapol and 4 mg thiomersal are dissolved in 33.4 g bidistilled water. The aqueous phase is heated to 60° C. and is added to the melt. The mixture is predispersed by probe sonication in a thermostatized vessel at 60° C. The predispersion is passed five times through a high pressure homogenizer (APV Gaulin Micron Lab 40)) thermostatized at 80° C. The homogenization pressure is 800 bar. The dispersion of PSMs is allowed to stand at room temperature for cooling. The mean particle size by number after preparation is 62.6 nm determined by PCS.

The physical state of the PSM dispersion of Example 20 is determined by DSC in a temperature range from 20 to 100° C. (FIG. 12b). The DSC thermogram of the dispersion does not reveal any transition peak pointing to the presence of amorphous particles. The absence of a second order phase transition (glas transition) hints at a liquid physical state of the dispersed particles.

Example 21

4.0 g Witepsol H35 (Hüls AG, Witten) is melted. 640 mg soya lecithin (Lipoid S 100, Lipoid KG) is dispersed in the melt by probe sonication (MSE Soniprep). 1.0 g glycerol, 160 mg sodium glycocholate and 4 mg thiomersal are dissolved in 34.2 g bidistilled water. The aqueous phase is heated to 60° C. and is added to the melt. The mixture is predispersed by probe sonication in a thermostatized vessel at 60° C. The predispersion is passed five times through a high pressure homogenizer (APV Gaulin Micron Lab 40) thermostatized at 80° C. The homogenization pressure is 800 bar. The dispersion of PSMs is allowed to stand at room temperature for cooling. The mean particle size by number after preparation is 106.9 nm determined by PCS.

The physical state of the PSM dispersion of Example 21 is determined by DSC in a temperature range from 20 to 100° C. (FIG. 12c). The DSC thermogram of the dispersion does not reveal any transition peak pointing to the presence of amorphous particles. The absence of a second order phase transition (glas transition) hints at a liquid physical state of the dispersed particles.

Example 22 (Predictive example)

4.0 g Witepsol H42 (Hüls AG, Witten) is melted. 800 mg soya lecithin (Lipoid S 100 Lipoid KG) is dispersed in the melt by probe sonication (MSE Soniprep). 40 mg taxol is dissolved in the melt. 1.0 g glycerol, 800 mg tyloxapol and 4 mg thiomersal are dissolved in 33.4 g bidistilled water. The aqueous phase is heated to 60° C. and is added to the melt. The mixture is predispersed by probe sonication in a thermostatized vessel at 60° C. The predispersion is passed five times through a high pressure homogenizer (APV Gaulin Micron Lab 40) thermostatized at 80° C. The homogenization pressure is 800 bar. The dispersion of PSMs is allowed to stand at room temperature for cooling.

Example 23 (Predictive example)

4.0 g Witepsol H42 (Hüls AG, Witten) is melted. 800 mg soya lecithin (Lipoid S 100, Lipoid KG) is dispersed in the melt by probe sonication (MSE Soniprep). 20 mg estramustin is dissolved in the melt. 1.0 glycerol, 800 mg tyloxapol and 4 mg thiomersal are dissolved in 33.4 g bidistilled water. The aqueous phase is heated to 60° C. and is added to the melt. The mixture is predispersed by probe sonication in a thermostatized vessel at 60° C. The predispersion is passed five times through a high pressure homogenizer (APV Gaulin Micron Lab 40) thermostatized at 80° C. The homogenization pressure is 800 bar. The dispersion of PSMs is allowed to stand at room temperature for cooling.

Example 24 (Predictive example)

4.0 g Witepsol H42 (Hüls AG, Witten) is melted. 800 mg soya lecithin (Lipoid S 100, Lipoid KG) is dispersed in the melt by probe sonication (MSE Soniprep). 200 mg ubidecarenone is dissolved in the melt. 1.0 g glycerol, 800 mg tyloxapol and 4 mg thiomersal are dissolved in 33.4 g bidistilled water. The aqueous phase is heated to 60° C. and is added to the melt. The mixture is predispersed by probe sonication in a thermostatized vessel at 60° C. The predispersion is passed five times through a high pressure homogenizer (APV Gaulin Micron Lab 40) thermostatized at 80° C. The homogenization pressure is 800 bar. The dispersion of PSMs is allowed to stand at room temperature for cooling.

Example 25 (Predictive example)

4.0 g ubidecarenone is melted in a thermostatized vessel at 80° C. 200 mg estramustin is dissolved in the melt. 500 mg sodium glycocholate and 1.0 g glycerol are dissolved in 32.1 g bidistilled water. 2.4 g lecithin is dispersed in the solution by sonication (Soniprep, MSE). The aqueous phase is heated to 80° C. and is added to the melt. The warm mixture is predispersed by sonication (Soniprep, MSE) for 3 min. The predispersion is homogenized at 800 bar for 5 cycles in a high pressure homogenizer type Micron Lab 40 (APV Gaulin) which is heated to 80° C. The dispersion is allowed to stand at room temperature for cooling.

Example 26 (Predictive example)

40 g ubidecarenone is melted in a thermostatized vessel at 80° C. 200 mg estramustin is dissolved in the melt. 500 mg sodium glycocholate and 1.0 g glycerol are dissolved in 32.1 g bidistilled water. 2.4 g lecithin is dispersed in the solution by sonication (Soniprep, MSE). The aqueous phase is heated to 80° C. and is added to the melt. The warm mixture is predispersed by sonication (Soniprep, MSE) for 3 min. The predispersion is homogenized at 800 bar for 5 cycles in a high pressure homogenizer type Micron Lab 40 (APV Gaulin) which is heated to 80° C. The dispersion is allowed to stand at room temperature for cooling.

Figure 1:
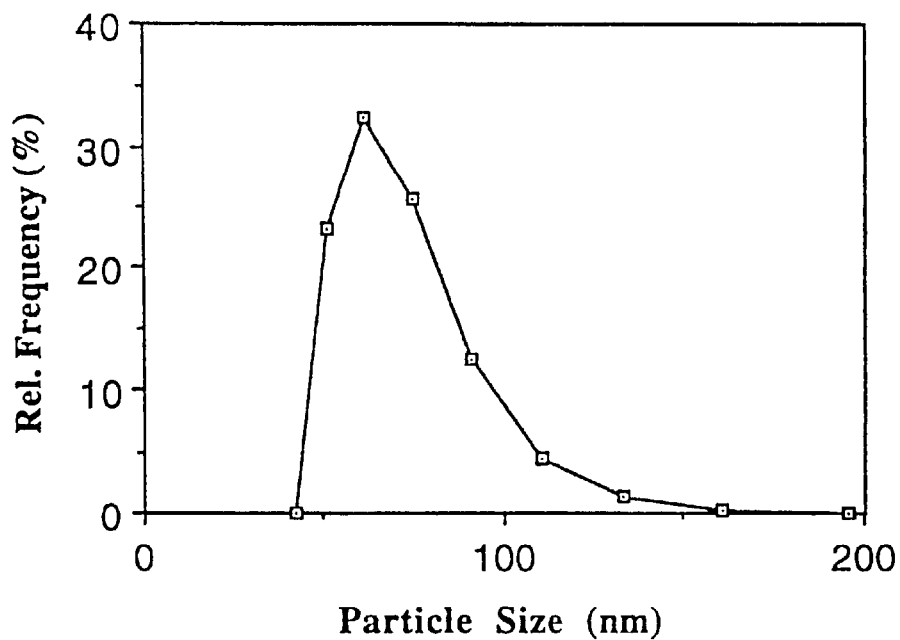
FIG. 1 Particle size distribution by number of ubidecarenone PSMs of Example 2 determined by photon correlation spectroscopy.
Figure 2:
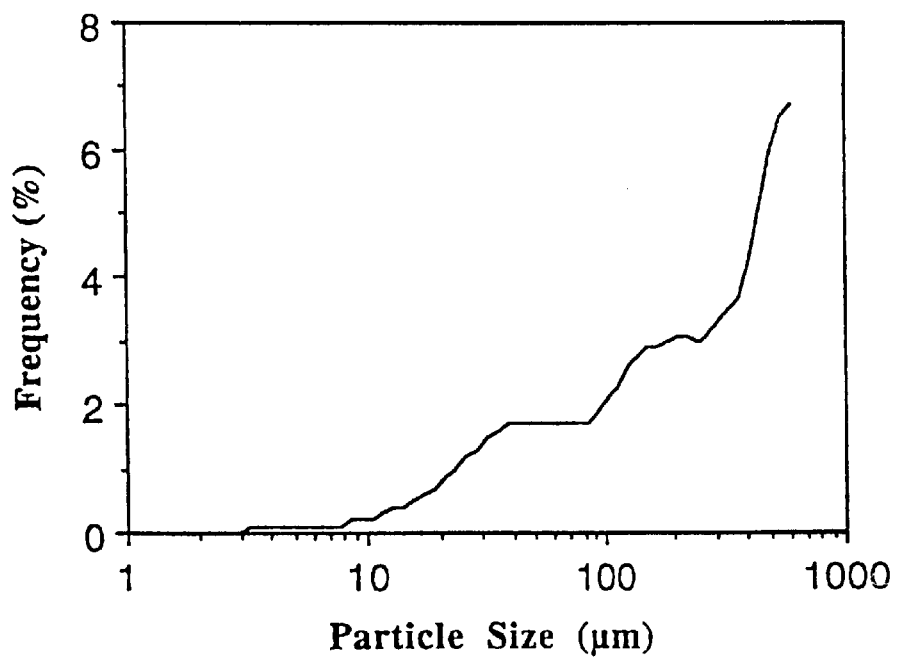
FIG. 2 Particle size distribution of crystalline ubidecarenone powder determined by laser diffractometry. For the measurement the powder was dispersed in an aqueous solution of 0.3% sodium glycocholate.
Figure 3:
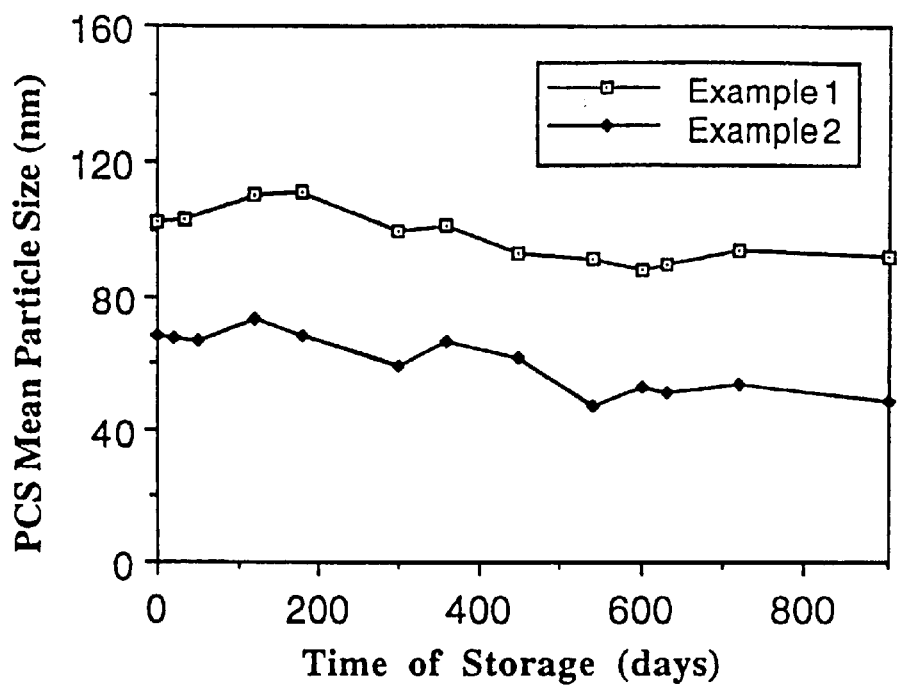
FIG. 3 Stability on storage of ubidecarenone PSMs of Examples 1 and 2: Dependence of the mean particle size (PCS number distribution) on storage time.
Figure 4:
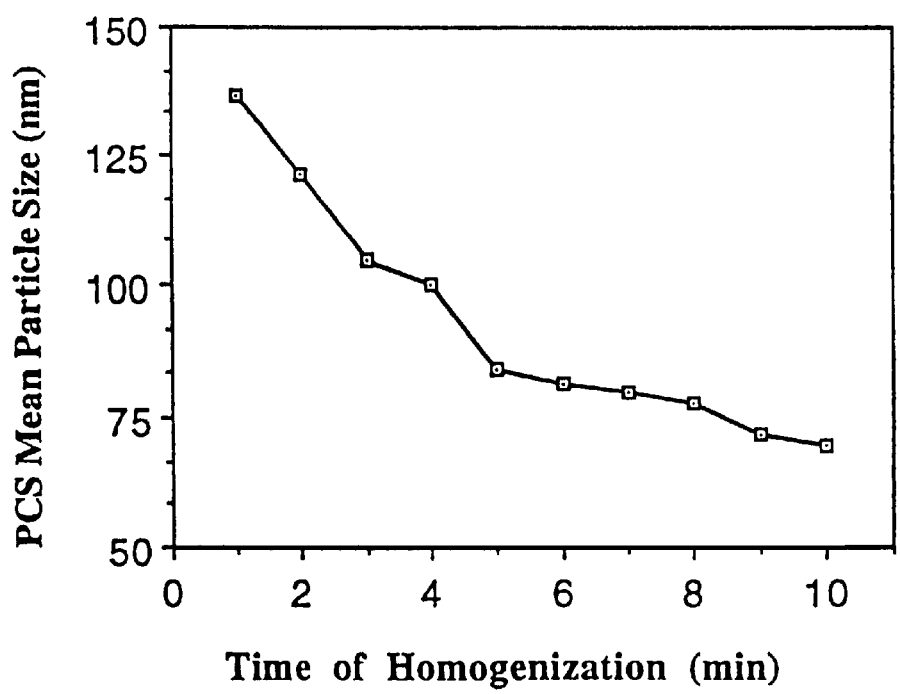
FIG. 4 Time course of homogenization in the Microfluidizer (Microfluidics Corp.): Dependence of the mean particle size of the ubidecarenone PSMs of Example 4 on homogenization time.
Figure 5:
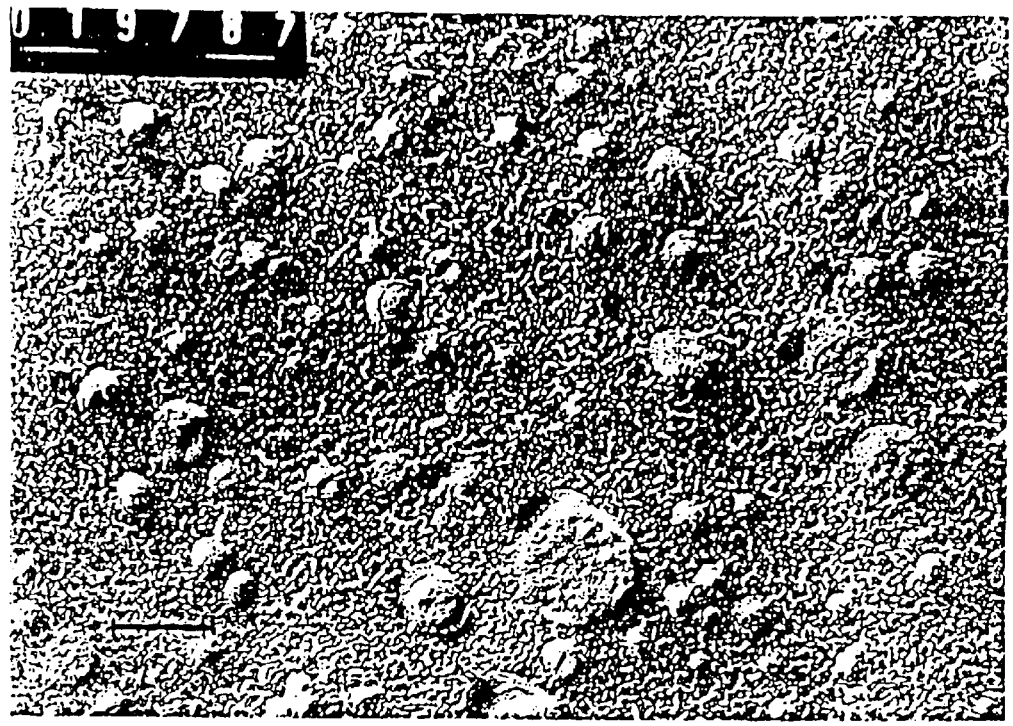
FIG. 5 Transmission electron microscopic picture of a freeze-fractured replicum of the ubidecarenone PSMs of Example 4 after 9 months storage at 4° C. The bar corresponds to 100 nm.
Figure 6:
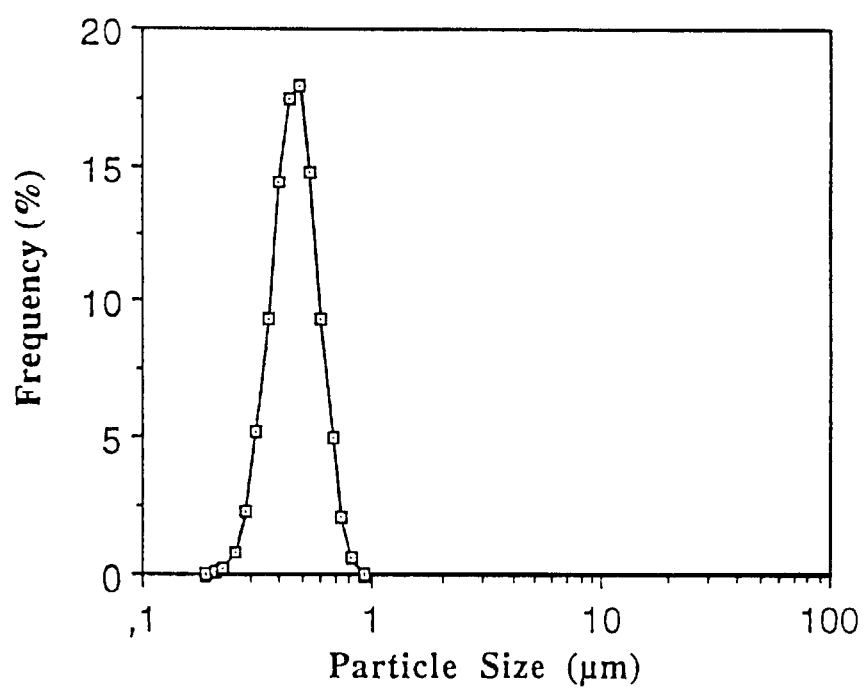
FIG. 6 Particle size distribution of the ubidecarenone PSMs of Example 5 determined by laser diffractometry.
Figure 7:
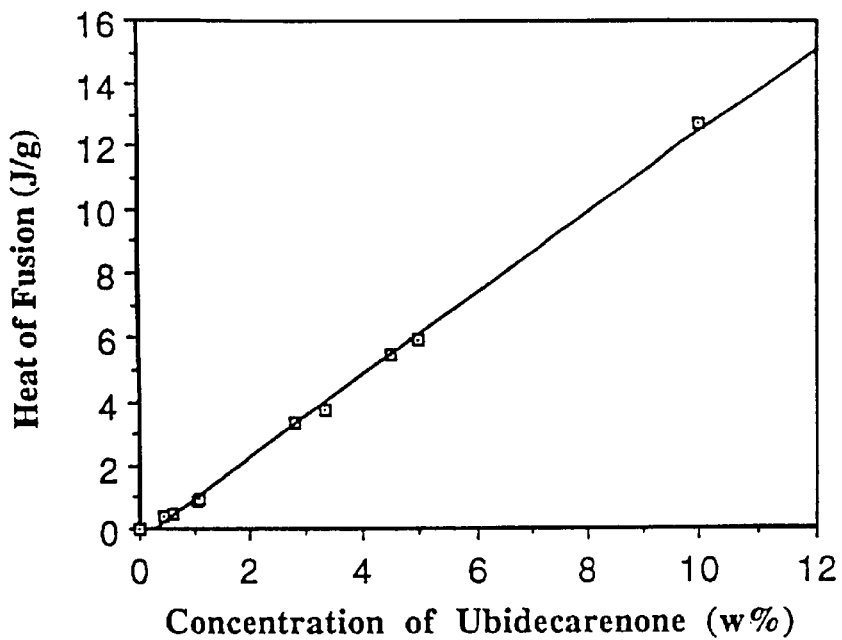
FIG. 7 DSC calibration curve of aqueous suspensions of crystalline ubidecarenone.
Figure 8:
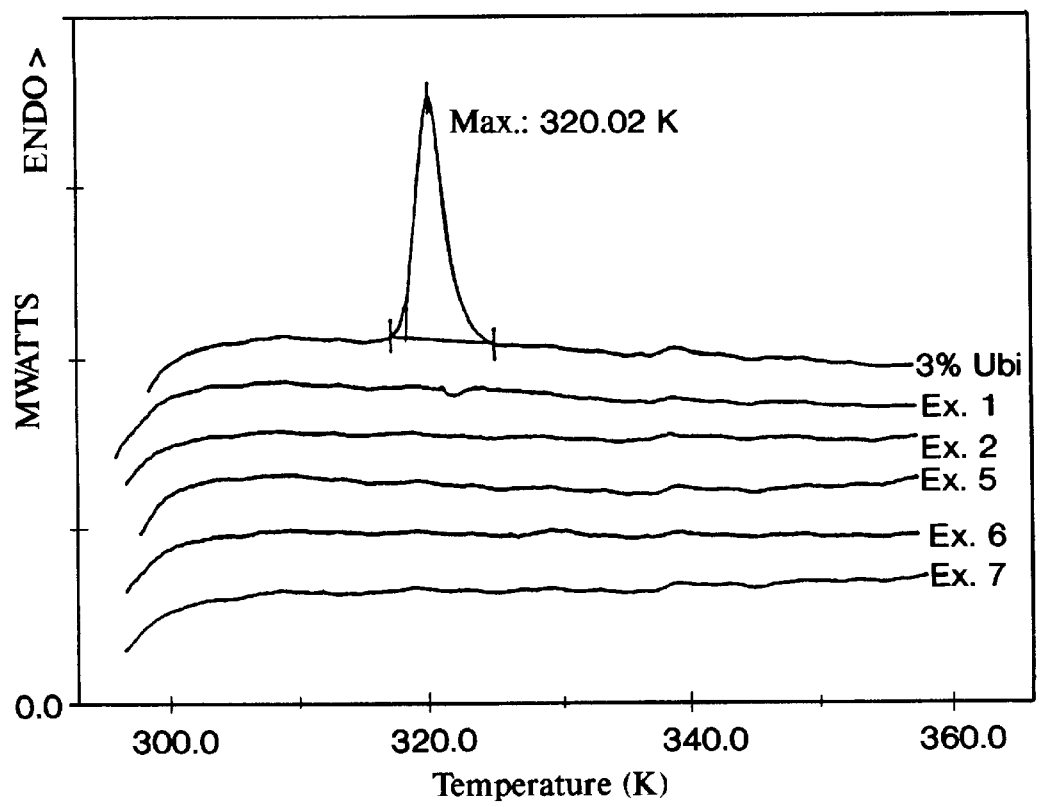
FIG. 8 DSC thermograms of the ubidecarenone PSMs of Examples 1, 2, 5, 6 and 7 compared to an aqueous suspension of 3% crystalline ubidecarenone.
Figure 9A:
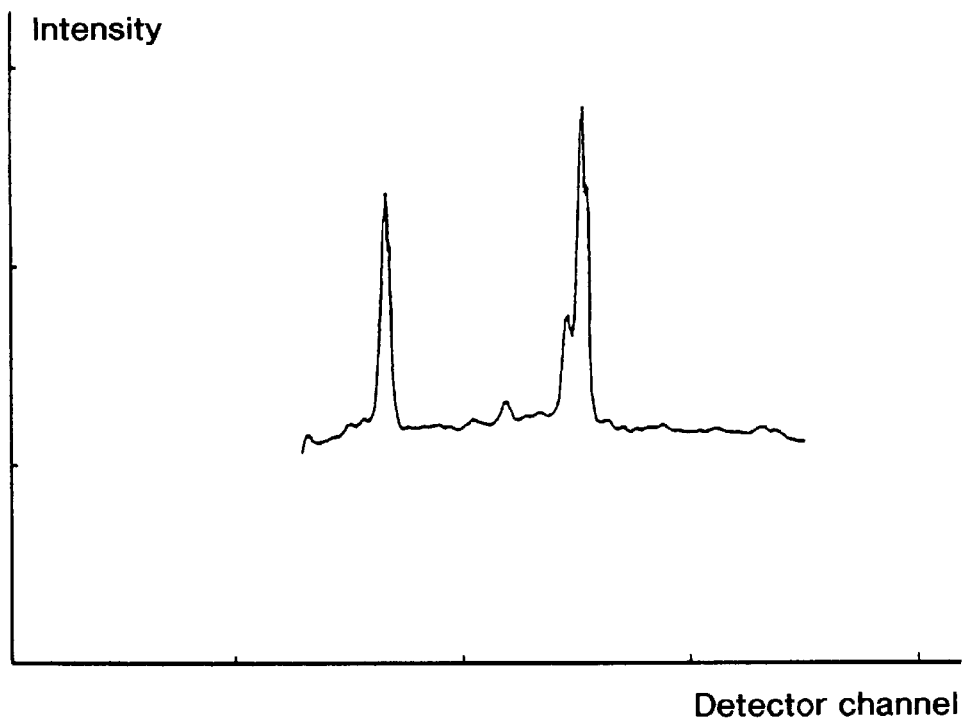
FIG. 9 Synchrotron radiation wide angle X-ray diffraction patterns of the powdered raw material ubidecarenone (a) and of the ubidecarenone PSMs of Example 1 (b).
Figure 9B:
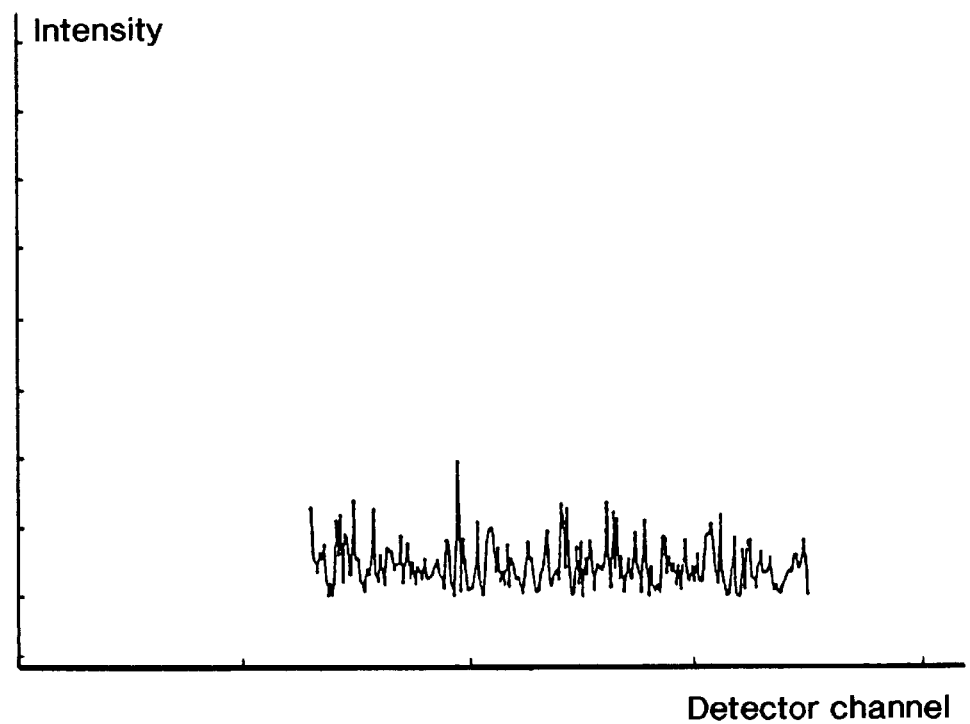
Figure 10A:
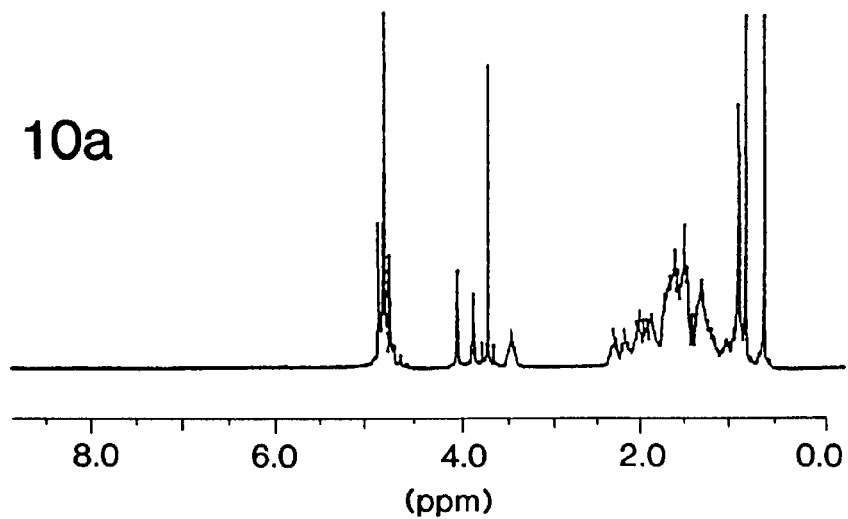
FIG. 10 Nuclear magnetic resonance spectroscopy: $^1$H NMR spectra of a) an aqueous solution of sodium glycocholate; b) a suspension of the powdered raw material ubidecarenone in an aqueous solution to sodium glycocholate heated to above the melting temperature of ubidecarenone; and c) the ubidecarenone PSMs of Example 10.
Figure 10B:
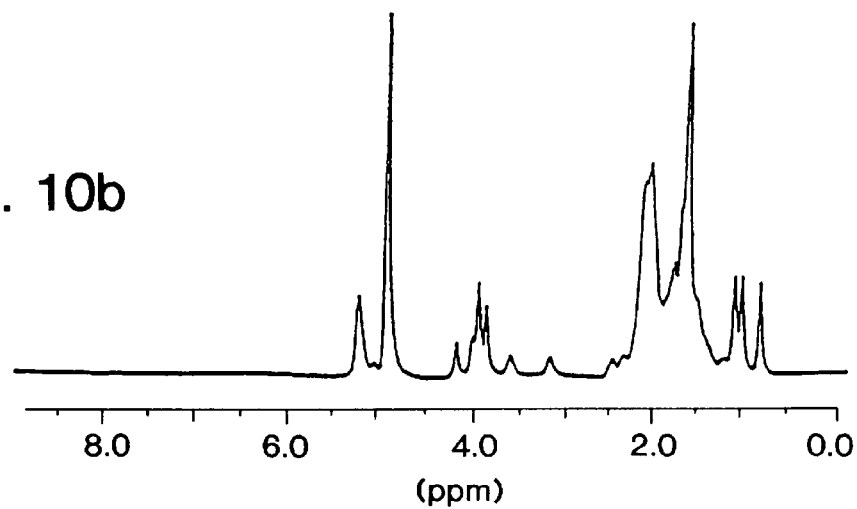
Figure 10C:
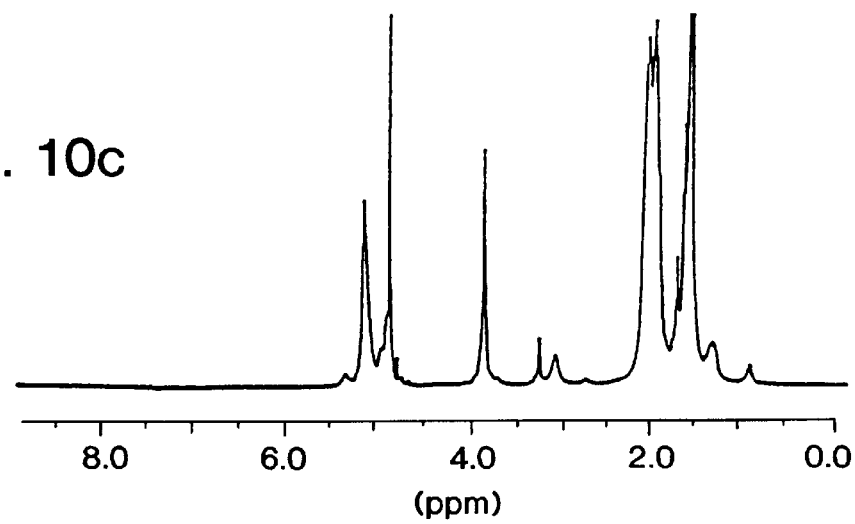
Figure 11:
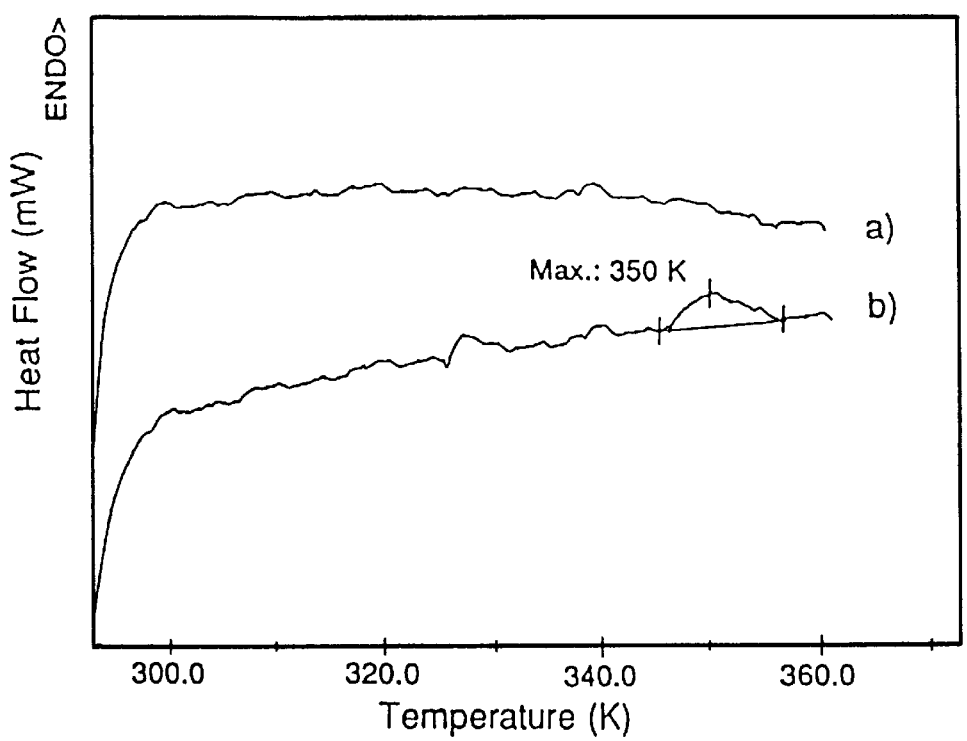
FIG. 11 DSC thermograms of a) the colecalciferol PSM dispersion of Example 15 after 14 months stored at 4° C.; and b) an aqueous suspension of 2% crystalline colecalciferol.
Figure 12:
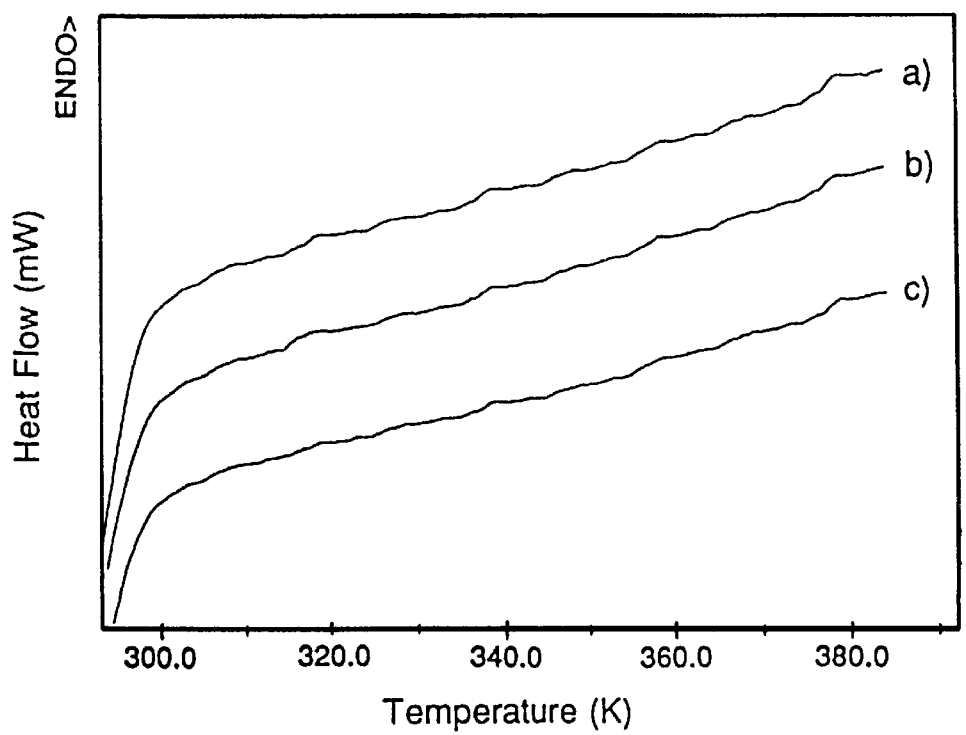
FIG. 12 DSC thermagrams of PSM dispersions of a) Example 19 stored at room temperature for 10 weeks; b) Example 20 stored at room temperature for 7 weeks; and c) Example 21 stored at room temperature for 10 weeks.

What is claimed is:

1. Particles having a mean particle size of between 30 and 500 nm comprising
   (a) a supercooled melt of a poorly water-soluble substance and
   (b) a stabilizing agent, which particles are the product of the process comprising melting said poorly water-soluble substance, and mixing and dispersing together said poorly water-soluble substance with said stabilizing agent,
   optionally in the presence of a dispersion medium, followed by cooling without crystallization.
2. The particles of claim 1, wherein the poorly water-soluble substance
   has a melting point below approximately 130° C. or its melting point can be decreased to below 130° C. by the addition of additives; and/or
   has a low recrystallization tendency.
3. The particles of claim 2, wherein recrystallization of the poorly water-soluble substance is impaired or inhibited or can be impaired or inhibited by the addition of additives.
4. The particles of claim 1, wherein the poorly water-soluble substance is ubidecarenone.
5. The particles of claim 1, wherein the poorly water-soluble substance is selected from the group consisting of vitamins, vitamin derivatives, low melting cholesterol esters, low melting triglycerides, and complex glyceride mixtures.
6. The particles of claim 1, wherein the stabilizing agent is an amphiphilic substance.
7. The particles of claim 1, wherein the stabilizing agent is an ionic or non-ionic surfactant.
8. The particles of claim 1, further containing an additive capable of
   decreasing the melting point of the poorly water-soluble substance, or
   impeding or inhibiting the re-crystallization of the poorly water-soluble substance after melting.
9. The particles of 1, further comprising a bioactive agent.
10. The particles of claim 9, wherein the bioactive agent is a therapeutic or diagnostic agent for use in a therapeutic treatment or a diagnostic method in a living human or animal body.
11. The particles of claim 9, wherein the bioactive agent is a herbicide, pesticide, insecticide, fungicide or fertilizer.
12. A composition comprising a dispersion medium and particles as defined in claim 1.
13. A composition comprising a dispersion medium and particles as defined in claim 9.
14. A composition comprising a dispersion medium and particles as defined in claim 10.
15. A composition comprising a dispersion medium and particles as defined in claim 11.
16. The composition of claim 12, wherein the dispersion medium is selected from a group consisting of water, ethanol, propylene glycol and methyl-isobutyl-ketone, or a mixture of the above.
17. The composition comprising a dispersion medium and particles as defined in claim 4.

* * * * *